(12) United States Patent  
Dariavach et al.

(10) Patent No.: US 9,504,676 B2
(45) Date of Patent: Nov. 29, 2016

(54) MOLECULES INHIBITING A METABOLIC PATHWAY INVOLVING THE SYK PROTEIN TYROSINE KINASE AND METHOD FOR IDENTIFYING SAID MOLECULES

(71) Applicants: Piona Dariavach, Montpellier (FR); Pierre Emile Ulysse Martineau, Saint Gely du Fesc (FR); Bruno Villoutreix, Paris (FR)

(72) Inventors: Piona Dariavach, Montpellier (FR); Pierre Emile Ulysse Martineau, Saint Gely du Fesc (FR); Bruno Villoutreix, Paris (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 53 days.

(21) Appl. No.: 14/059,406

(22) Filed: Oct. 21, 2013

(65) Prior Publication Data

US 2014/0179679 A1 Jun. 26, 2014

Related U.S. Application Data

(63) Continuation of application No. 12/937,189, filed as application No. PCT/FR2009/000414 on Apr. 8, 2009, now abandoned.

(30) Foreign Application Priority Data

Apr. 9, 2008 (FR) ..................... 08/01959

(51) Int. Cl.
| | |
|---|---|
| A61K 31/426 | (2006.01) |
| A61K 31/167 | (2006.01) |
| A61K 31/18 | (2006.01) |
| A61K 31/33 | (2006.01) |
| A61K 31/5377 | (2006.01) |
| A61K 31/553 | (2006.01) |
| A61K 31/53 | (2006.01) |
| A61K 31/517 | (2006.01) |
| A61K 31/506 | (2006.01) |
| A61K 31/502 | (2006.01) |
| A61K 31/495 | (2006.01) |
| A61K 31/451 | (2006.01) |
| A61K 31/445 | (2006.01) |
| A61K 31/435 | (2006.01) |
| A61K 31/427 | (2006.01) |
| A61K 31/41 | (2006.01) |
| A61K 31/404 | (2006.01) |
| A61K 31/351 | (2006.01) |
| A61K 31/343 | (2006.01) |
| A61K 31/4015 | (2006.01) |
| A61K 31/4025 | (2006.01) |
| A61K 31/4035 | (2006.01) |
| A61K 31/4155 | (2006.01) |

(Continued)

(52) U.S. Cl.
CPC .......... *A61K 31/426* (2013.01); *A61K 31/167* (2013.01); *A61K 31/18* (2013.01); *A61K 31/33* (2013.01); *A61K 31/343* (2013.01); *A61K 31/351* (2013.01); *A61K 31/404* (2013.01); *A61K 31/4015* (2013.01); *A61K 31/4025* (2013.01); *A61K 31/4035* (2013.01); *A61K 31/41* (2013.01); *A61K 31/4155* (2013.01); *A61K 31/4162* (2013.01); *A61K 31/4178* (2013.01); *A61K 31/4196* (2013.01); *A61K 31/427* (2013.01); *A61K 31/435* (2013.01); *A61K 31/445* (2013.01); *A61K 31/4439* (2013.01); *A61K 31/451* (2013.01); *A61K 31/4525* (2013.01); *A61K 31/4704* (2013.01); *A61K 31/495* (2013.01); *A61K 31/502* (2013.01); *A61K 31/506* (2013.01); *A61K 31/517* (2013.01); *A61K 31/53* (2013.01); *A61K 31/5377* (2013.01); *A61K 31/553* (2013.01); *A61K 45/06* (2013.01); *G01N 2333/186* (2013.01); *G01N 2333/9121* (2013.01)

(58) Field of Classification Search
CPC .. A61K 31/426; A61K 31/167; A61K 31/18; A61K 31/33; A61K 31/343; A61K 31/351; A61K 31/404; A61K 31/41; A61K 31/427; A61K 31/435; A61K 31/445; A61K 31/451; A61K 31/495; A61K 31/502; A61K 31/506; A61K 31/517; A61K 31/53; A61K 31/5377; A61K 31/553

See application file for complete search history.

(56) References Cited

U.S. PATENT DOCUMENTS

| | | | |
|---|---|---|---|
| 2008/0146453 | A1 | 6/2008 | Martineau |
| 2010/0210632 | A1 | 8/2010 | Kai et al. |

FOREIGN PATENT DOCUMENTS

| | | |
|---|---|---|
| WO | WO 01/09134 A1 | 2/2001 |
| WO | WO 03/030897 A1 | 4/2003 |

(Continued)

OTHER PUBLICATIONS

Kambayashi T., Koretzky F.A. (2007) "Proximal signaling events in Fc$_{epsilon}$RI-mediated mast cell activation" J Allergy Clin Immunol, vol. 119, No. 3, p. 544-552.

(Continued)

*Primary Examiner* — Rebecca Anderson
(74) *Attorney, Agent, or Firm* — John P. White; Cooper & Dunham LLP

(57) ABSTRACT

The present invention relates to the C-13 molecule (methyl 2-{5-[(3-benzyl-4-oxo-2-thioxo-1,3-thiazolidin-5-ylidene) methyl]-2-furyl}-benzoate) and to organic molecules functionally equivalent to the C-13 molecule, capable of inhibiting the binding of an antibody or antibody fragment with the human Syk protein tyrosine kinase, to the use of these molecules for the production of medicaments for the prevention or treatment of diseases dependent on metabolic pathways involving Syk, and also to a method for identifying such molecules.

11 Claims, 14 Drawing Sheets

Figure 1:
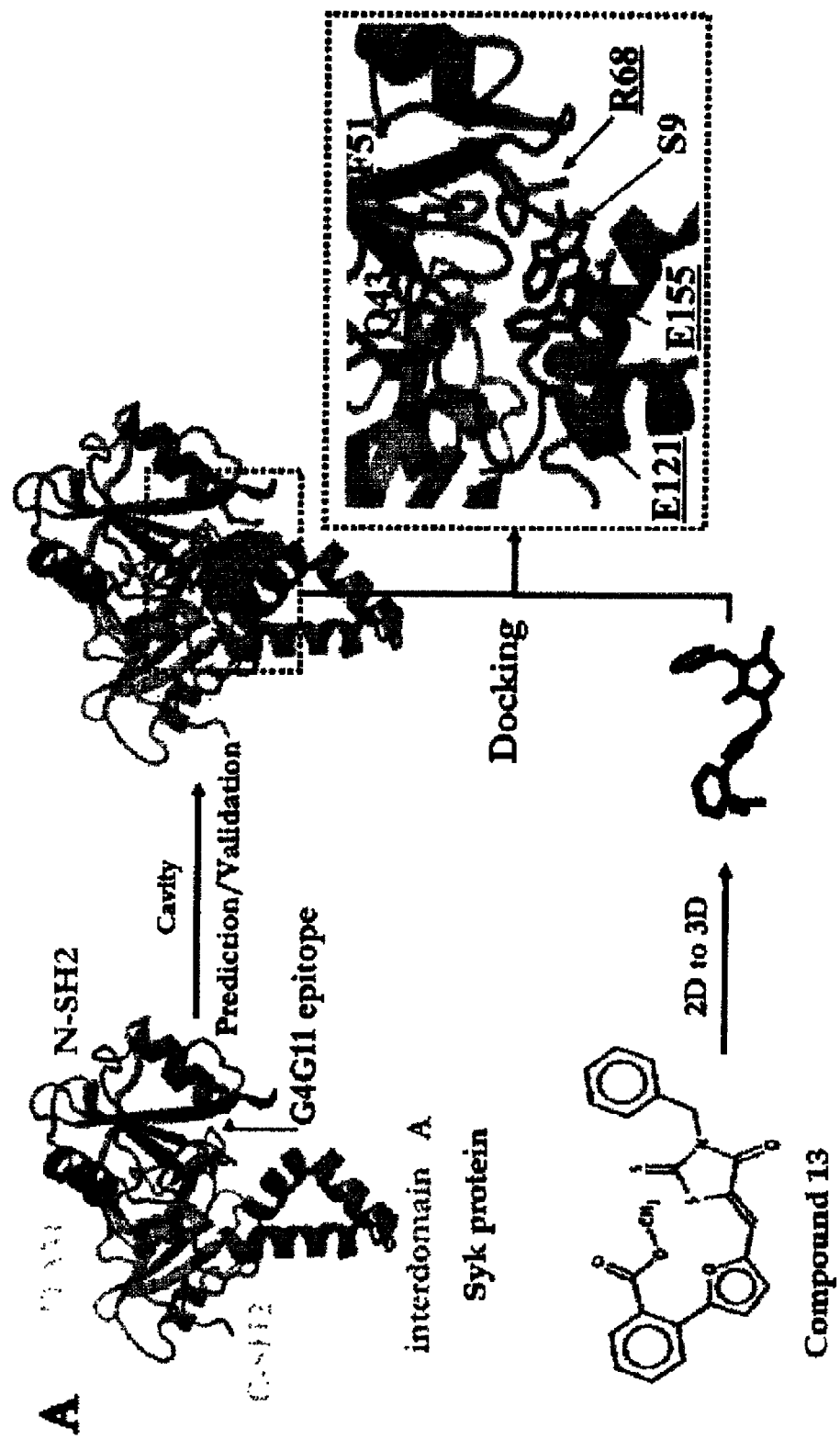
Figure 1:
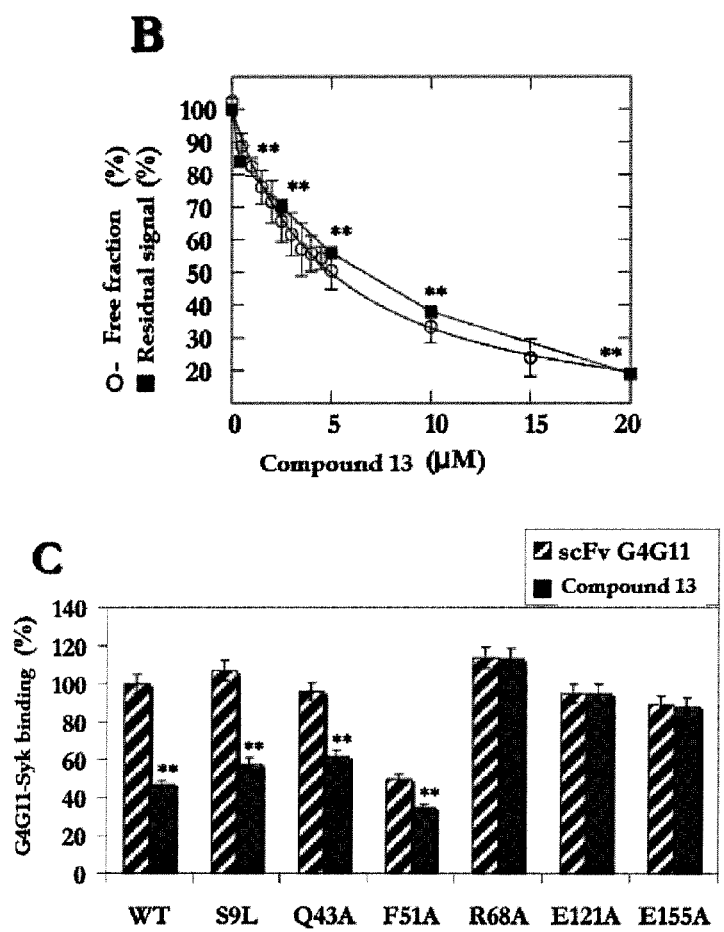

(51) Int. Cl.
| | |
|---|---|
| A61K 31/4162 | (2006.01) |
| A61K 31/4178 | (2006.01) |
| A61K 31/4196 | (2006.01) |
| A61K 31/4525 | (2006.01) |
| A61K 31/4704 | (2006.01) |
| A61K 31/4439 | (2006.01) |
| A61K 45/06 | (2006.01) |

(56) References Cited

FOREIGN PATENT DOCUMENTS

| | | |
|---|---|---|
| WO | WO 03/057695 A1 | 7/2003 |
| WO | WO 2004/089415 A2 | 10/2004 |
| WO | WO 2006/066846 A1 | 6/2006 |
| WO | WO 2008/033798 A2 | 3/2008 |

OTHER PUBLICATIONS

Rivera J., Gilfillan A.M. (2006) "Molecular regulation of mast cell activation" J Allergy Clin Immunol, vol. 117, No. 6, p. 1214-1225, quiz 26.
Costello P.S., Turner M., Walters A.E., Cunningham C.N., Bauer P.H., Downward J., et al. (1996) Critical role for the tyrosine, kinase inase Syk in signaling through the high affinity IgE receptor of mast [abstract].
Wong W.S.F., Leong K.P. (2004) "Tyrosine kinase inhibitors: a new approach for asthma" Biochimica et Biophysica Acta,1697, p. 53-69.
Turner M., Schweighoffer E., Colucci F., Di Santo J.P., Tybulewicz V.L. (2000) "Tyrosine kinase Syk: essential functions for immunoreceptor signalling" Immunology Today, vol. 21, No. 3, p. 148-154.
Coopman P.J., Mueller S.C. (2006) "The Syk tyrosine kinase: a new negative regulator in tumor growth and progression" Cancer Letters, 241, p. 159-173.
Dauvillier S., Mérida P., Visintin M., Cattaneo A., Bonnerot C., Dariavach P. (2002) "Intracellular singlechain variable fragments directed to the Src homology 2 domains of Syk partially inhibit $Fc_{epsilon}RI$ signaling in the RBL-2H3 cell line" The Journal of Immunology, 169, p. 2274-2283.
Peneff C., Lefranc M-P., Dariavach P. (2000) "Characterisation and specificity of two single-chain Fv antibodies directed to the protein tyrosine kinase Syk" Journal of Immunological Methods, vol. 236, p. 105-115.
Lobato M.N., Rabbitts T.H. (2003) "Intracellular antibodies and challenges facing their use as therapeutic agents" TRENDS in Molecular, vol. 9, No. 9, p. 390-396.
Latour S., Bonnerot C., Fridman W.H., Daeron M. (1992) "Induction of tumor necrosis factor-alpha production by mast cells via $Fc_{gamma}R$—Role of the $Fc_{gamma}RIII_{gamma}$ subunit" J Immunol. vol. 149, No. 6, p. 2155-2162 [abstract].
Dombrowicz D., Flamand V., Miyajima l., Ravetch J.V., Galli S.J., Kinet J-P. (1997) "Absence of $Fc_{epsilon}RI_{alpha}$ chain results in upregulation of $Fc_{gamma}RIII$-dependent mast cell degranulation and anaphylaxis—Evidence of competition between $Fc_{epsilon}RI$ and $Fc_{gamma}RIII$ for limiting amounts of FcR$_{beta}$ and $_{gamma}$ chains" The Journal of Clinical Investigation, vol. 99, No. 5, p. 915-925.
Laurie A.T.R., Jackson R.M. (2005) "Q-SiteFinder: an energy-based method for the prediction of protein-ligand binding sites" Bioinformatics, vol. 21, No. 9, p. 1908-1916.
An J., Totrov M., Abagyan R. (2004) "Comprehensive identification of 'druggable' protein ligand binding sites" Genome Informatics, vol. 15, No. 2, p. 31-41.
Venkatachalam C.M., Jiang X., Oldfield T., Waldman M. (2003) "LigandFit: a novel method for the shape-directed rapid docking of ligands to protein active sites" Journal of Molecular Graphics and Modelling, vol. 21, p. 289-307.

Jain A.N. (2003) "Surflex: fully automatic flexible molecular docking using a molecular similarity-based search engine" J. Med. Chem, 46, p. 499-511.
Frank R., Overwin H. (1996) "SPOT synthesis: Epitope analysis with arrays of synthetic peptides prepared on cellulose membranes" Methods in Molecular Biology, vol. 66, p. 149-169 [abstract].
Fritterer K., Wong J., Grucza R.A., Chan A.C., Waksman G. (1998) "Structural basis for Syk tyrosine kinase ubiquity in signal transduction pathways revealed by the crystal structure of its regulatory SH2 domains bound to a dually phosphorylated ITAM peptide" J. Mol. Biol., 281, p. 523-537.
Nadler M.J.S., Matthews S.A., Turner H., Kinet J-P. (2000) "Signal transduction by the high-affinity immunoglobulin E receptor $Fc_{epsilon}RI$: coupling form to function" Advances in Immunology, vol. 76, p. 325-355.
Parravicini V., Gadina M., Kovarova M., Odom S., Gonzalez-Espinosa C., Furumoto Y., et al. (2002) "Fyn kinase initiates complementary signals required for IgE-dependent mast cell degranulation" Nature Immunology, vol. 3, No. 8, p. 741-748.
Rameh L.E., Rhee S.G., Spokes K., Kazlauskas A., Cantley L.C., Cantley L.G. (1998) "Phosphoinositide 3-kinase regulates phospholipase $C_{gamma}$-mediated calcium signaling" The Journal of Biological Chemistry, vol. 3, No. 8, p. 741-748.
Saitoh S-I., Odom S., Gomez G., Sommers C.L., Young H.A., Rivera J., Samelson L.E. (2003) "The four distal tyrosines are required for LAT-dependent signaling in $Fc_{epsilon}RI$-mediated mast cell activation" The Journal of Experimental Medicine, vol. 198, No. 5, p. 891-843.
Silverman M.A., Shoag J., Wu J., Koretzky G.A. (2006) "Disruption of SLP-76 interaction with Gads inhibits dynamic clustering of SLP-76 and $Fc_{epsilon}RI$ signaling in mast cells" Molecular and Cellular Biology, vol. 26, No. 5, p. 1826-1838.
Hendricks-Taylor L.R., Motto D.G., Zhang J., Siraganian R.P., Koretzky G.A. (1997) "SLP-76 is a substrate of the high affinity IgE receptor-stimulated protein tyrosine kinases in rat basophilic leukemia cells" The Journal of Biological Chemistry, vol. 272, No. 2, p. 1363-1367.
Takata M., Kurosaki T. (1996) "A role for Bruton's tyrosine kinase in B cell antigen receptor-mediated activation of phospholipase $C-_{gamma}2$" J Exp Med, vol. 184, p. 31-40.
Law C-L., Chandran K.A., Sidorenko S.P., Clark E.A. (1996) "Phospholipase $C-_{gamma}1$ interacts with conserved phosphotyrosyl residues in the linker region of Syk and is a substrate for Syk" Molecular and Cellular Biology, vol. 16, No. 4, p. 1305-1315.
Pivniouk V.I., Martin T.R., Lu-Kuo J.M., Katz H.R., Oettgen H.C., Geha R.S. (1999) SLP-76 deficiency impairs signaling via the high-affinity IgE receptor in mast cells J Clin Invest, vol. 103, No. 12, p. 1737-1743.
Kettner A., Pivniouk V., Kumar L., Falet H., Lee J-S., Mulligan R., et al. (2003) "Structural requirements of SLP-76 in signaling via the high-affinity immunoglobulin E receptor ($Fc_{epsilon}RI$) in mast cells"Molecular and Cellular Biology, vol. 23, No. 7, p. 2395-2406.
Manetz T.S., Gonzalez-Espinosa C., Arudchandran R., Xirasagar S., Tybulewicz V., et al. (2001) "Vav1 regulates phospholipase $C_{gamma}$ activation and calcium responses in mast cells" Molecular and Cellular Biology, vol. 21, No. 11, p. 3763-3774.
Wilson B.S., Pfeiffer J.R., Oliver J.M. (2001) "$Fc_{epsilon}RI$ signaling observed from the inside of the mast cell membrane" Molecular Immunology, vol. 38, p. 1259-1268.
Wu J.N., Jordan M.S., Silverman M.A., Peterson E.J., Koretzky G.A. (2004) "Differential requirement for adapter proteins Src homology 2 domain-containing leukocyte phosphoprotein of 76 kDa and adhesion- and degranulation-promoting adapter protein in $Fc_{epsilon}RI$ signaling and mast cell function" The Journal of Immunology, vol. 172, p. 486-496.
Barker S.A., Caldwell K.K., Pfeiffer J.R., Wilson B.S. (1998) "Wortmannin-sensitive phosphorylation, translocation and activation of $PLC_{gamma}1$, but not $PLC_{gamma}2$, in antigen-stimulated RBL-2H3 mast cells" Molecular Biology of the Cell, vol. 9, p. 483-496.
Fluckiger A-C., Li Z., Kato R.M., Wahl M.I., Ochs H.D., Longnecker R., et al. (1998) "Btk/Tec kinases regulate sustained increases in intracellular $Ca^{2+}$ following B-cell receptor activation" The EMBO Journal, vol. 17, No. 7, p. 1973-1985.

(56) References Cited

OTHER PUBLICATIONS

Scharenberg A.M., Ei-Hillal O., Fruman D.A., Beitz L.O., Li Z., Lin S., et al. (1998) "Phosphatidylinositol-3,4,5-trisphosphate (Ptdlns-3,4,5-P3)/Tec kinase-dependent calcium signaling pathway: a target for SHIP-mediated inhibitory signals" The EMBO Journal, vol. 17, No. 7, p. 1961-1972.

Wen R., Jou S-T., Chen Y., Hoffmeyer A., Wang D. (2002) "Phospholipase $C_{gamma}2$ is essential for specific functions of $Fc_{epsilon}R$ and $Fc_{gamma}R$" The Journal of Immunology, vol. 169, p. 6743-6752.

Qi Q., August A. (2007) "Keeping the (Kinase) Party Going: SLP-76 and ITK Dance to the Beat" Sci STKE, 396, pe39 (p. 1-7).

Mocsai A., Zhou M., Meng F., Tybulewicz V.L., Lowell C.A. (2002) "Syk is required for integrin signaling in neutrophils" Immunity, vol. 16, p. 547-558.

Matsumoto T., Guo Y-J., Ikejima T., Yamada H. (2003) "Induction of cell cycle regulatory proteins by murine B cell proliferating pectic polysaccharide from the roots of *Bupleurum falcatum* L" Immunology letters, 89, p. 111-118.

Okkenhaug K., Bilancio A., Farjot G., Priddle H., Sancho S., Peskett E., et al. (2002) "Impaired B and T cell antigen receptor signaling in p110delta PI 3-kinase mutant mice" Science, vol. 297, p. 1031-1034.

Gell PGH, Coombs RRA (1963) Eds. Clinical Aspects of Immunology. 1st ed. Oxford, England: Blackwell [abstract].

Berge S.M. et al. (1977) "Pharmaceutical Salts" Journal of Pharmaceutical Science, vol. 66, No. 66, No. 1, p. 1-19.

Floquet N., Richez C., Durand P., Maigret B., Badet B., Badet-Denisot M-A. (2007) "Discovering new inhibitors of bacterial glucosamine-6P synthase (GlmS) by docking simulations" Bioorganic & Medicinal Chemistry Letters, vol. 17, p. 1966-1970.

Choi H.Y., Yan G.H. (2009) "Silibinin Attenuates Mast Cell-Mediated Anaphylaxis-Like Reactions" Biol. Pharm. Bull. , vol. 32, No. 5, p. 868-875.

Choi H.Y., Yan G.H. (2009) "Anti-allergic effects of scoparone on mast cell-mediated allergy model" Phytomedicine, vol. 16, p. 1089-1094.

El-Agamy D.S. (2012) "Anti-Allergic effects of nilotinib on mast-cell mediated anaphylaxis like reactions" European Journal of Pharmacology, vol. 680, p. 115-121.

Finn D. F . , Walsh J. J (2013) "Twenty-first century mast cell stabilizers" British Journal of Pharmacology, vol. 170, 170, p. 23-37.

Han S. J., et al. (2007) "Magnolol and Honokiol: Inhibitors against Mouse Passive Cutaneous Anaphylaxis Reaction and Scratching Behaviors" Biol . Pharm. Bull. , vol. 30, No. 11, p. 2201-2203.

Malfait A-M. , et al. (1999) "The β2-Adrenergic Agonist Is a Potent Suppressor of Established Collagen-Induced Arthritis: Mechanisms of Action" The Journal of Immunology, vol. 162, p. 6278-6283.

Reddy G.D. , et al. (2012) "Antiallergic Activity Profile In Vitro RBL-2H3 and In Vivo Passive Cutaneous Anaphylaxis Mouse Model of New Sila- Substitued 1, 3, 4-Oxadiazole" Journal of Medicinal Chemistry, vol. 55, p. 6438-6444.

International Search Report issued by the International Searching Authority (ISA/EPO) on Feb. 19, 2010 in connection with PCT International Application No. PCT/FR2009/000414 with English translation.

Notification of Transmittal of International Preliminary Report on Patentability (Chapter I of the Patent Cooperation Treaty), including an International Preliminary Report on Patentability and English translation of Written Opinion of the International Searching Authority, issued by the International Searching Authority (ISA/EPO) on Oct. 21, 2010 in connection with PCT International Application No. PCT/FR2009/000414 U.S. Pat. No. 7,713,698, issued to Ju et al. on May 11, 2010.

Mazuc, E., Villoutreix, B., Malbec, O., Roumier, T., Fluery, S., Leonetti, J., Dombrowicz, D., Daëron, M., Martineau, P. & Daravach, P. (2008). A Novel Druglike Spleen Tyrosine Kinase Binder Prevents Anaphylactic Shock When Administered Orally. *Mecahnisms of Allergy and Clinical Immunology*, 122, 1, 188-196.

Carlson et al. Chemistry & Biology 13, 825-837, Aug. 2006.

Carlson et al. Chemistry & Biology 13, supplemental data. Aug. 2006.

Golub et al., Science (1999), Vo. 286, 531-537.

Lala and Orucevic, Cancer and Metastasis Reviews (1998), 17(1), 91-16.

Feb. 27, 2013 Amendment in Response to Sep. 27, 2012 Office Action and Petition for Four-Month Extension of Time.

Apr. 22, 2013 Office Action in connection with U.S. Appl. No. 12/931,189.

Sep. 27, 2012 Office Action in connection with U.S. Appl. No. 12/937,189.

Figure 2:
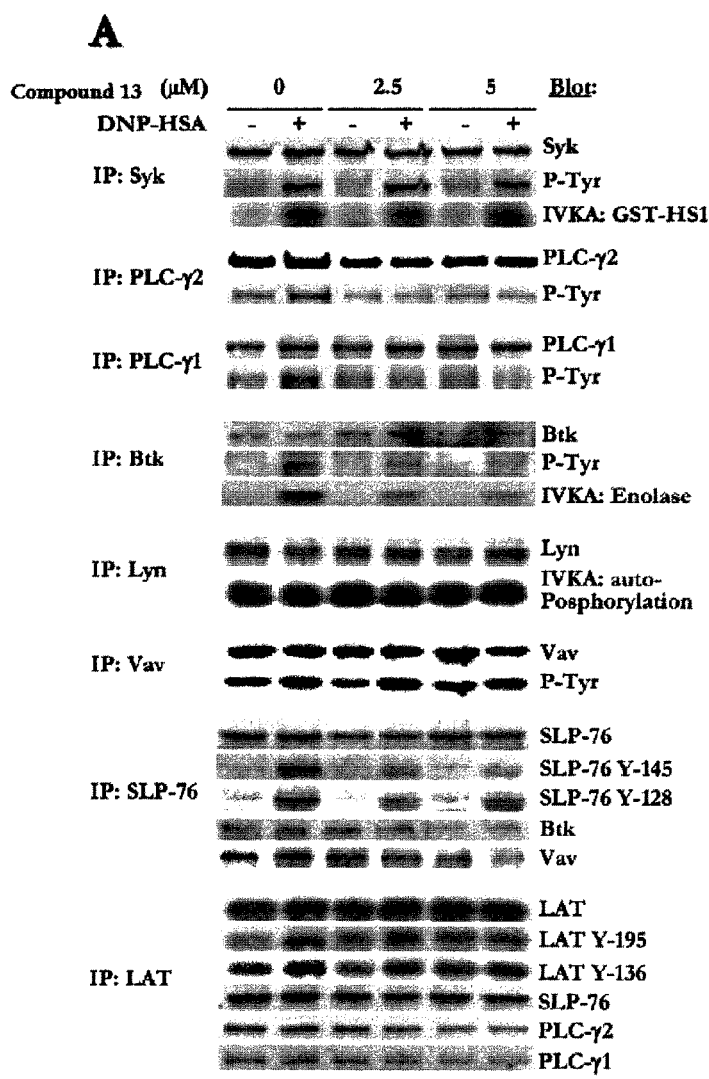

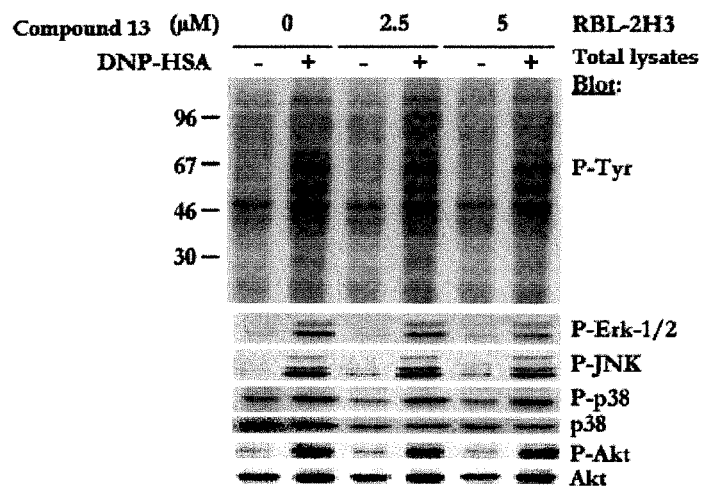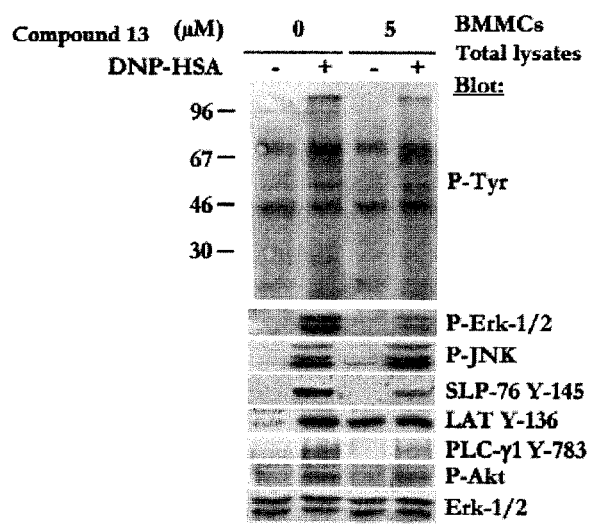
Figure 2 (continued)

A maqvqlqesg pglvkpsdtl sltcavsgys isssnwwgwi rqppgkglew igyiyhsgst    60
yynpslksrv tisvdksknq fslklssvta adtavyycar nvgfhdwgqg tlvtvssggg   120
gsggggsggs alqsvltqpp sasgtpgqrv tiscsgsssn igsnyvywyq qlpgtapkll   180
iyrnnqrpsg vpdrfsgsks gtsaslaisg lrsedeadyy caawddslas pvfgggtklt   240
vlgaaahhhh hhgaaeqkli seedlngaa                                    269

B maqvqlqesg pglvkpsdtl sltcavsgys isssnwwgwi rqppgkglew igyiyhsgst    60
yynpslksrv tisvdksknq fslklssvta adtavyycar nvgfhdwgqg tlvtvssggg   120
gsggggsggs alqsvltqpp sasgtpgqrv tiscsgsssn igsntvnwyq qlpgtapkll   180
iysnnqrpsg vpdrfsgsks gtsaslaisg lqsedeadyy caawddslfg avfgggtklt   240
vlgaaahhhh hhgaaeqkli seedlngaa                                    269

Figure 7

A

```
  1 massgmadsa nhlpfffgni treeaedylv qggmsdglyl lrgsrnylgg falsvahgrk
 61 ahhytierel ngtyaiaggr thaspadlch yhsqesdglv cllkkpfnrp qgvqpktgpf
121 edlkenlire yvkqtwnlqg qaleqaiisq kpqlekliat tahekmpwfh gkisreeseq
181 ivligsktng kflirardnn gsyalcllhe gkvlhyridk dktgklsipe gkkfdtlwql
241 vehysykadg llrvltvpcq kigtqgnvnf ggrpqlpgsh patwsaggii sriksysfpk
301 pghrksspaq gnrqestvsf npyepelapw aadkgpqrea lpmdtevyes pyadpeeirp
361 kevyldrkll tledkelgsg nfgtvkkgyy qmkkvvktva vkilkneand palkdellae
421 anvmqqldnp yivrmigice aeswmlvmem aelgplnkyl qqnrhvkdkn iielvhqvsm
481 gmkyleesnf vhrdlaarnv llvtqhyaki sdfglskalr adenyykaqt hgkwpvkwya
541 pecinyykfs sksdvwsfgv lmweafsygq kpyrgmkgse vtamlekger mgcpagcpre
601 mydlmnlcwt ydvenrpgfa avelrlrnyy ydvvn
```

B

```
  1 magsavdsan hltyffgnit reeaedylvq ggmtdglyll rqsrnylggf alsvahnrka
 61 hhytiereln gtyaisggra haspadlchy hsqepdglic llkkpfnrpp gvqpktgpfe
121 dlkenlirey vkqtwnlqgq aleqaiisqk pqlekliatt ahekmpwfhg nisrdeseqt
181 vligsktngk flirardnsg syalcllheg kvlhyridrd ktgklsipeg kkfdtlwqlv
241 ehysykpdgl lrvltvpcqk igaqmghpgs pnahpvtwsp ggiisriksy sfpkpghkkp
301 appqgsrpes tvsfnpyept ggpwgpdrgl qrealpmdte vyespyadpe eirpkevyld
361 rslltledne lgsgnfgtvk kgyyqmkkvv ktvavkilkn eandpalkde llaeanvmqq
421 ldnpyivrmi giceaeswml vmemaelgpl nkylqqnrhi kdkniielvh qvsmgmkyle
481 esnfvhrdla arnvllvtqh yakisdfgls kalradenyy kaqthgkwpv kwyapeciny
541 ykfssksdvw sfgvlmweaf sygqkpyrgm kgsevtamle kgermgcpag cpremydlmn
601 lcwtydvenr pgftavelrl rnyyydvvn
```

Figure 8

MOLECULES INHIBITING A METABOLIC PATHWAY INVOLVING THE SYK PROTEIN TYROSINE KINASE AND METHOD FOR IDENTIFYING SAID MOLECULES

This application is a §371 national stage of PCT International Application No. PCT/FR2009/000414, filed Apr. 8, 2009, designating the United States, and claims priority of French Patent Application No 0801959, filed Apr. 9, 2008.

The present invention relates to organic molecules capable of inhibiting the binding of an antibody or antibody fragment with human Syk tyrosine kinase protein, the use of said molecules for producing medicinal products for the prevention and treatment of conditions dependent on metabolic pathways involving Syk, and a method for identifying such molecules.

Figure 9:
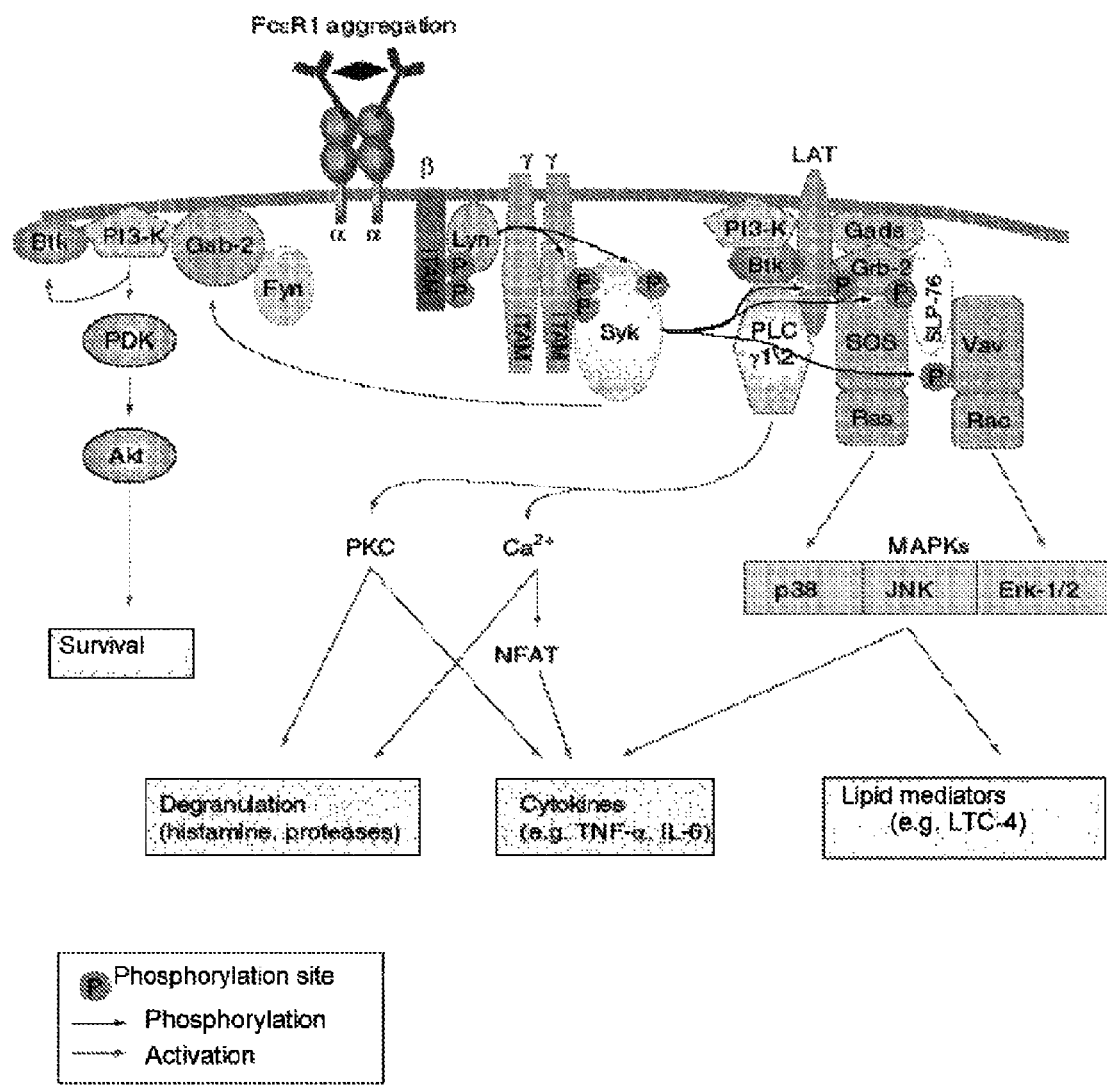

Syk ("Spleen tyrosine kinase") Tyrosine Kinase protein (PKT) is a cytoplasmic protein which is a key mediator in immunoreceptor-dependent signalling in the cells involved in inflammation such as B lymphocytes, mast cells, macrophages and neutrophils. In mast cells and basophils, crosslinking of the FcεRI receptor (receptor with high affinity for immunoglobulin E) with IgE and antigens induces phosphorylation of FcεRI ITAM ("Immunoreceptor Tyrosine-based Activation Motif") motifs so as to form a binding site for Syk which is then activated. The activated Syk protein in turn phosphorylates numerous substrates, including LAT ("linker for activation of T cells"), SLP-76 ("Src homology 2 (SH2) domain-containing leukocyte protein of 76 kD") and Vav adapter proteins, resulting in the activation of a plurality of signalling cascades, such as those of PLC-γ (phospholipase Cγ), PI3K ("phosphatidylinositol 3-kinase"), Erk ("extracellular signal-regulated kinase"), JNK ("c-jun N-terminal kinase") and p38 (see FIG. 9). These cascades eventually give rise to the degranulation, synthesis and release of lipid mediators and the production and secretion of cytokines, chemokines and growth factors by mast cells and basophils[1,2].

Syk protein is thus recognised as a potential pharmaceutical target, particularly for the treatment of type I hypersensitivity reactions including allergic rhinitis, urticaria, asthma and anaphylaxis due to its critical position upstream from immunoreceptor signalling complexes regulating the inflammatory response in leukocytes. The fact that Syk regulates FcεRI signalling positively[3], particularly suggests that it could be an excellent target for the treatment of allergic disorders. Furthermore, due to the central role thereof. In FcεRI-dependent signalling, interacting pharmaceutically with Syk could prove to be more advantageous than the conventional use of antihistamines or leukotriene receptor agonists inhibiting a single step downstream from the complex cascades contributing to the acute and chronic symptoms associated with allergic conditions.

Pharmacological inhibitors of Syk kinase activity having a therapeutic potential, such as, in particular, Syk-specific anti-sense oligonucleotides in the form of aerosols or small molecules interfering with Syk activity such as ER-27139, BAY-613606, piceatannol and R112 have already been developed[1, 4]. However, if multiple types of cells expressing Syk are considered, potential side effects associated with systemic exposure of the immune system to medicinal products targeting the Syk kinase domain need to be taken into consideration. Indeed, Syk protein is widely distributed in various cell types, it is thus essential to account for the adverse effects of the inhibition thereof on varied physiological functions such as cell differentiation, adhesion and proliferation[5,6].

The inventors identified Syk protein inhibitors which act by preventing the interaction thereof with the natural cellular partners thereof rather than by targeting the catalytic site thereof, particularly compound C-13 and compounds 1 to 87 given in table 1.

The present invention relates to the molecule C-13 (methyl 2-{5-[(3-benzyl-4-oxo-thioxo-1,3-thiazolidin-5-ylidene)methyl]-2-furyl}benzoate) having the formula

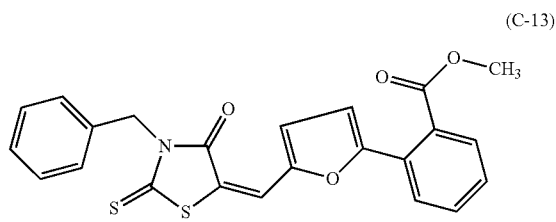 [SMILES: COC(=O)c1ccccc1-c1ccc(/C=C2/SC(=S)N(Cc3ccccc3)C2=O)o1]

(C-13)

as a medicinal product for the prevention or treatment of a condition dependent on a metabolic pathway involving Syk in humans or animals.

The present invention further relates to functionally equivalent organic molecules to molecule C-13, binding with Syk tyrosine kinase protein and particularly molecules capable of inhibiting by at least 5%, preferably at least 10%, for example at least 15, 20, 25, 30, 35, 40, 45, 50, 55, 60, 65, 70, 75, 80 or 85% in vitro binding of (i) antibody fragment G4G11 (SEQ ID No. 2), or
(ii) antibody fragment G4E4 (SEQ ID No. 3), or
(iii) an antibody or antibody fragment which binds with human Syk tyrosine kinase protein on an epitope comprising at least one of residues 65 to 74 of the amino acid sequence of human Syk tyrosine kinase protein represented by the sequence SEQ ID No. 1, or
(iv) an antibody or antibody fragment which binds with human Syk tyrosine kinase protein and inhibiting by at least 10% the binding of antibody fragments G4G11 or G4E4 with human Syk tyrosine kinase protein (SEQ ID No. 1)

with human Syk tyrosine kinase protein or with any of the variants thereof in animals, for example murine Syk tyrosine kinase protein wherein the sequence is illustrated in FIG. 8B (SEQ ID No. 4), as a medicinal product for the prevention or treatment of a condition dependent on a metabolic pathway involving Syk in humans or animals.

The term "functionally equivalent molecule" refers to a molecule, for example an organic molecule having a molecular weight between 50 and 2500 Da, capable of resulting in the same effect in vitro in an intra or extracellular medium or in vivo, optionally with a different intensity, than a given molecule. In particular, within the scope of the present invention, the term "functionally equivalent molecule to molecule C-13" refers to a molecule capable of producing the same effect in vitro in an intra or extracellular medium or in viva optionally with a different intensity, on human tyrosine kinase protein as represented by sequence SEQ ID No. 1 (FIG. 8A) as molecule C-13. In particular, it refers to molecules inhibiting the binding of Syk with another protein produced on the Syk region comprising the SH2 domains thereof. More specifically, these molecules do not affect the kinase enzyme activity of Syk. For example, this consists of molecules capable of inhibiting the interaction of Syk tyrosine kinase protein with antibody fragment G4G11 (SEQ ID No. 2), antibody fragment G4E4 (SEQ ID No. 3), or an antibody or antibody fragment binding with the same epitope as antibody fragment G4G11 or G4E4 on human Syk protein (SEQ ID No. 1).

The term "percentage of inhibition" of the binding of an antibody or antibody fragment with Syk protein, particularly refers to the ratio [(A−B)/(A×100)], where A consists of the intensity of a signal proportional to the quantity of an antibody or antibody fragment bound with Syk protein in the absence of a molecule according to the invention and B the intensity of the same signal in the presence of a molecule according to the invention under the same conditions. The inhibition of the binding of an antibody or antibody fragments with Syk protein may particularly be demonstrated in vitro by an antibody displacement test based on the ELISA technique as described for example in international application WO 2005106481. This test may be performed for example according to the protocol described in example 3-2) hereinafter.

The term "Syk variants in animals" refers to the genes of various animal species, for example mouse, rat, dog, cat or another mammal, coding for a protein having a strong sequence homology or identity with human Syk protein as represented by the sequence SEQ ID No. 1 (see FIG. 8A), for example a protein having at least 70, 75, 80, 85, 90 or 95% sequence homology or identity with the sequence SEQ ID No. 1 of human Syk protein, having the same tyrosine kinase activity and involved in the same functional cascades as same, particularly in the functional cascade giving rise to mast cell degranulation. It may particularly refer to orthologous genes, i.e. genes found in different organisms, having evolved from the same ancestral gene following speciation events.

The present invention also relates to the pharmaceutically acceptable salts, and if applicable, stereoisomers and racemates of C-13 or of equivalent molecules according to the invention.

The term "pharmaceutically acceptable salts" refers to relatively non-toxic inorganic and organic acid or basic addition salts preserving the biological activity of the molecules according to the invention. Examples of pharmaceutically acceptable salts are particularly described in S. M. Berge et al., "Pharmaceutical Salts", J. Pharm. Sci, 1977, 66:p. 1-19$^{40}$. The pharmaceutically acceptable addition salts of molecules according to the invention may for example be hydrobromide, hydrochloride, sulphate, bisulphate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulphamate, malonate, salicylate, propionate, methylenebis-b-hydroxynaphthoate, gentisic acid, isethionate, di-p-toluoyltartrate, methanesulphonate, ethane-sulphonate, benzenesulphonate, p-toluenesulphonate, cyclohexyl sulphamate and quinateslaurylsulphonate salts, and equivalents. Other pharmaceutically acceptable salts which may be suitable include metal salts, for example pharmaceutically acceptable alkaline metal or alkaline-earth salts, such as sodium, potassium, calcium or magnesium salts.

These pharmaceutically acceptable salts may be prepared in situ during the final molecule isolation and purification. Alternatively, the acid or basic addition salts may be prepared by reacting the purified molecule separately in the acid or basic form thereof with a base or an organic or inorganic acid and by isolating the salt formed. For example, a pharmaceutically acceptable acid addition salt may be prepared by reacting a molecule according to the invention with a suitable organic or inorganic acid (such as for example hydrobromic, hydrochloric, sulphuric, nitric, phosphoric, succinic, maleic, formic, acetic, propionic, fumaric, citric, tartaric, lactic, benzoic, salicylic, glutamic, aspartic, p-toluene-sulphonic, benzene-sulphonic, methane-sulphonic, ethane-sulphonic, hexanoic or naphthalene-sulphonic acids such as 2-naphthalene sulphonic acid), optionally in a suitable solvent such as an organic solvent. A basic addition salt may, when a suitable acid group is present, be prepared by reacting a molecule according to the invention with a suitable organic or inorganic base (for example triethylamine, ethanol-amine, triethanol-amine, choline, arginine, lysine or histidine), optionally in a suitable solvent such as an organic solvent. The salts thus generated may then be isolated by means of crystallisation and filtration.

In some embodiments, pharmaceutically acceptable salts are preferred in that they provide the molecules according to the invention with superior stability or solubility, facilitating the formulation thereof.

According to one particularly preferred embodiment, the organic molecules according to the invention bind with Syk tyrosine kinase protein at a site located outside the catalytic domain thereof.

Also preferably, the organic molecules according to the invention have a molecular weight between 50 and 2500 Dalton, for example between 50 and 2000 Da, between 50 and 1500 Da or between 50 and 1000 Da.

According to one particular embodiment, the molecules according to the invention are capable of inhibiting, by at least 5%, preferably by at least 10%, the binding of an antibody or antibody fragment binding with human Syk tyrosine kinase protein on an epitope comprising at least two, preferably at least 3, 4 or 5, for example 5, 6, 7, 8, 9 or 10 of residues 65 to 74 of the amino acid sequence of human Syk tyrosine kinase protein (SEQ ID No. 1), with human Syk tyrosine kinase. According to one preferred embodiment, the antibody or antibody fragment binds with human Syk tyrosine kinase protein on the same epitope as antibody fragment G4G11 or antibody fragment G4E4 on human Syk tyrosine kinase protein, the sequence of which is illustrated by SEQ ID No. 1.

According to a further particular embodiment, the molecules according to the invention are capable of inhibiting, by at least 5%, preferably by at least 10%, the binding of an antibody or antibody fragment which binds to with Syk tyrosine kinase protein and inhibits, by at least 15%, preferably by at least 20, 30, 40, 50, 60, 70 or 80%, the binding of antibody fragments G4G11 or G4E4 with human Syk tyrosine kinase protein (SEQ ID No. 1), with human Syk tyrosine kinase protein.

Preferably, the molecules according to the invention bind with human Syk protein on a three-dimensional cavity comprising the Arginine residue situated in position 68 and the two glutamic acid residues situated in positions 121 and 155 of the Syk protein, the sequence of which is illustrated by SEQ ID No. 1. Preferably still, the three-dimensional cavity further comprises the Serine residue situated in position 9, the Glutamine residue situated in position 43, the Phenylalanine residue situated in position 51, the Isoleucine residue situated in position 66, the Glutamate residues situated in position 67 and 69, the Leucine residue situated in position 70, the Asparagine residue situated in position 71, the Glycine residue situated in position 72, the Threonine residue situated in position 73, the Tyrosine residue situated in position 74 and the Alanine residue situated in position 75 of human Syk protein, the sequence of which is illustrated by SEQ ID No. 1.

More preferably, the in vitro affinity, measured by the dissociation constant (or Kd), of the molecules according to the invention for Syk protein, is less than 100 µM, more preferably, less than 50 µM, and particularly preferably, less than 25 µM. The affinity of the molecules according to the invention for Syk protein is, for example, between 0.01 and 100 µM, between 0.1 and 50 µM or between 0.5 and 25 µM. The dissociation constant of the molecules according to the invention with respect to Syk protein may particularly be measured in vitro by means of fluorescence spectroscopy (or spectrofluorometry).

The present invention further relates to the use of a molecule according to the Invention for producing a medicinal product for the prevention or treatment of a condition dependent on a metabolic pathway involving Syk in humans or animals.

According to one particularly preferred embodiment, the molecules or salts according to the invention are used for producing a medicinal product for the prevention or treatment of type I hypersensitivity reactions.

The term "hypersensitivity" refers to an unsuitable or excessive immune response to an allergen, for example pollen, dust, animal hairs or certain foods, with effects ranging from moderate allergic reaction (skin rash, rhinitis, conjunctivitis, etc.) to severe systemic reactions potentially resulting in anaphylactic shock and potentially life-threatening in some cases. Immediate and delayed hypersensitivity reactions are classified in types I and IV respectively of the classification defined by Gell and Coombs (Gell PGH, Coombs RRA, eds. Clinical Aspects of Immunology. 1st ed. Oxford, England: Blackwell; 1963[39]). According to this classification, "type I (or atopic or anaphylactic) hypersensitivity" is an immediate allergic reaction associated with exposure to a specific antigen or allergen, for example by swallowing, inhalation, injection or direct contact, and the triggering of immunoglobulin E (IgE) secretion by plasma cells. The IgE binds with the Fc receptors found on the surface of tissue mast cells and blood basophils. Subsequent exposure to the sensitised mast cells and basophils to the same allergen gives rise to the degranulation of the cells having the corresponding IgE and the release of mediators such as histamine, leukotriene or prostaglandins acting on the surrounding tissues, particularly giving rise to vasodilation and smooth muscle contraction. The reactions may be local or systemic and the symptoms vary from moderate irritation to sudden death due to anaphylactic shock. Examples of conditions caused by type I hypersensitivity include allergic asthma, allergic conjunctivitis, allergic rhinitis (hay fever), anaphylaxis, angioedema, urticaria, eosinophilia, allergies to antibiotics such as penicillin or cephalosporin. "Type II hypersensitivity" or "antibody-dependent immune response" is a reaction generally requiring from a few hours to one day, associated with interactions between antibodies (IgG, IgM) and an antigen on the surface of the cells of the patient carrying this antigen, giving rise to the destruction of these cells and the proliferation of B lymphocytes, producing antibodies against the antigen. "Type III hypersensitivity" or "immune complex disease" is a reaction developing over a number of hours, days or weeks, associated with the presence of similar quantities of antibodies and antigens giving rise to the formation of immune complex not suitable for evacuation circulating in the vessels, the deposition thereof on the walls of said vessels and giving rise to local or systemic inflammatory responses. "Type IV hypersensitivity" or "cell-mediated immunity" or "delayed hypersensitivity reaction" is an immune reaction generally requiring two to three days to develop and not associated with an antibody response but with the formation of a complex between cells which express a major histocompatibility complex I or II antigen and T lymphocytes giving rise to the release of lymphokines and/or cytotoxicity mediated by T lymphocytes.

Preferably, the molecules or salts according to the invention are used for producing medicinal products for the prevention or treatment of type I hypersensitivity reactions which inhibit IgE-dependent mast cell degranulation. More preferably, the molecules according to the invention are capable of inhibiting by 50% in vitro mast cell degranulation, at a concentration (IC50) between 1 ng/ml and 1 mg/ml, for example at a concentration between 1 ng/ml and 500 µg/ml, between 1 ng/ml and 250 µg/ml, between 1 ng/ml and 100 µg/ml, between 1 ng/ml and 50 µg/ml, between 1 ng/ml and 10 µg/ml, between 1 ng/ml and 5 µg/ml or between 1 ng/ml and 2 µg/ml. Also preferably, a quantity between 1 nM and 1 mM, for example between 1 nM and 100 nM, between 10 nM and 100 nM or between 1 nM and 10 nM, of a molecule according to the invention is capable of inhibiting mast cell degranulation by 50% in vitro.

More preferably, the metabolic pathway involving Syk on which the molecules or salts according to the invention is a mast cell or basophil activation pathway.

More preferably, the condition on which the molecules or salts according to the invention act is allergic asthma, allergic conjunctivitis, allergic rhinitis, anaphylaxis, angioedema, urticaria, eosinophilia or an allergy to an antibiotic.

According to one preferred embodiment, the molecules or salts according to the invention have no effect on the metabolic pathways involving human Syk protein (SEQ ID No. 1) other than those giving rise to mast cell degranulation and/or type I hypersensitivity reactions. More preferably, the molecules or salts according to the invention have no effect on the antibody response following immunisation by a thymus-dependent antigen or on Syk-dependent neutrophil recruitment.

Syk tyrosine kinase protein is also found on the surface of B lymphocytes, T lymphocytes, neutrophils, eosinophlis, NK cells, platelets, erythrocytes, osteoclasts, epithelial cells or cancer cells. According to one alternative embodiment, the metabolic pathway involving Syk on which the molecules or salts according to the Invention act is a B lymphocyte, T lymphocyte, neutrophil, eosinophil, NK cell, platelet, erythrocyte, osteoclast, epithelial cell or cancer cell activation pathway. According to this embodiment, the condition on which the molecules or salts according to the invention act may thus be rheumatoid arthritis, an autoimmune disease, inflammation or cancer.

According to one particular embodiment, the molecules or salts according to the invention may be used in combination with another therapeutic molecule. For example, it may consist of a therapeutic molecule also used for the prevention or treatment of a condition dependent on a metabolic pathway involving Syk or, on the other hand, a therapeutic molecule used for the prevention or treatment of a condition not dependent on a metabolic pathway involving Syk. According to one preferred embodiment, the molecules or salts according to the invention are used in combination with a molecule used for the treatment of allergy or type I hypersensitivity or for the treatment of the symptoms associated therewith. More preferably, the molecules or salts according to the invention are used in combination with epinephrine (or adrenaline), an H1 antihistamine, for example diphenhydramine, meclizine, fluphenazine, perphenazine, prochlorperazine, trifluoperazine, acrivastine, astemizole, cetirizine, levocetirizine, fexofenadine, loratadine, desloratadine, mizolastine, azelastine, levocabastine, olopatadine, cromoglicate, nedocromil, a non-steroidal anti-inflammatory drug (NSAID) or a steroidal anti-inflammatory drug, for example cortisone, hydrocortisone (or cortisol), cortisone acetate, prednisone, prednisolone, methylprednisolone, dexamethasone, betamethasone, triamcinolone, beclometasone, fludrocortisone, deoxycorticosterone acetate or aldosterone. According to a further preferred embodiment, the molecules or salts according to the invention are used in combination with an allergic desensitisation (or anti-allergic vaccination), i.e. a treatment based on regular increasing doses of an allergen. According to one particular embodiment, the molecule according to the invention is not used in combination with a glucocorticoid receptor agonist.

The molecules or salts according to the invention may be administered by any administration route, particularly by the oral, sublingual, nasal, ocular, local, intravenous, intraperitoneal, subcutaneous routes, by aerosol or by inhalation.

The molecules or salts according to the Invention may particularly be administered to adult, child or newborn human patients. The molecules or sales according to the invention may also be administered to animal patients, particularly mammals such as dogs, cats, rats, mice.

In particular, the molecules or salts according to the invention are administered to a human patient at doses determined particularly on the basis of the patients condition, medical history and age, for example doses between 0.1 mg/kg and 200 mg/kg.

The present invention also relates to a therapeutic method for the treatment or prevention of a condition dependent on a metabolic pathway involving Syk in a human or animal patient comprising the administration of a molecule according to the invention to the patient at doses, intervals and periods determined particularly on the basis of the patient's condition, medical history and age.

According to one particularly preferred embodiment, the molecules according to the invention are selected from all the molecules consisting of C-13, molecules No. 1 to 87 given in table No. 1 and the molecules having any of the following formulas (I), (II), (III) or (IV):

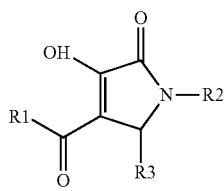
(I)

where
R1 is an optionally substituted aromatic group, or an optionally substituted heterocycle comprising at least one S, O or N atom;
R2 is an optionally substituted aromatic group, an optionally substituted heterocycle, an optionally saturated carbon chain, comprising an amine group, an optionally saturated carbon chain comprising an optionally substituted aromatic group or an optionally saturated carbon chain comprising an optionally substituted heterocycle comprising at least one S, O or N atom;
R3 is an optionally substituted phenyl, 2-pyridinyl, 3-pyridinyl or 4-pyridinyl group;

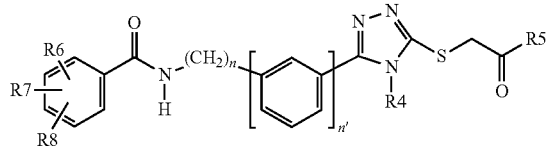
(II)

where
n=0 or 1; n'=0 or 1;
R4 is an optionally saturated carbon chain comprising 1 to 5 carbon atoms, optionally substituted with an aromatic group;
R5 is an optionally substituted aromatic group or an optionally substituted amine group;
R6 is a hydrogen atom, alkoxy group, alkyl group or halogen;
R7 is a hydrogen atom, alkoxy group, alkyl group or halogen;
R8 is a hydrogen atom, alkoxy group, alkyl group or halogen;

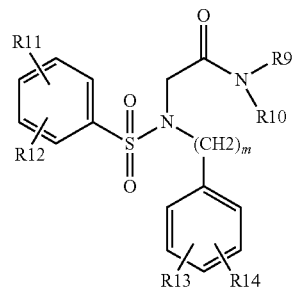
(III)

where
m=0, 1 or 2;
R9 is a hydrogen atom and R10 is an optionally substituted phenyl group, or R9 and R10 are part of the same optionally substituted heterocycle, or R9 and R10 are part of the same optionally substituted aromatic group;
R11 is a hydrogen atom, alkoxy group or alkyl group;
R12 is a hydrogen atom, alkoxy group or alkyl group;
R13 is a hydrogen atom or an alkyl or alkoxy group;
R14 is a hydrogen atom or an alkyl or alkoxy group;

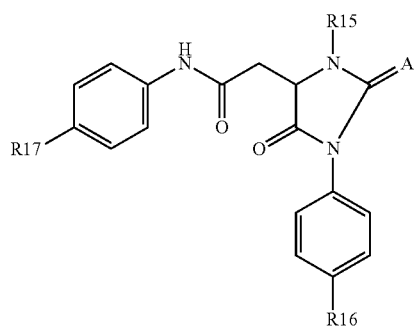
(IV)

where

A is an oxygen or sulphur atom;

R15 is an optionally saturated carbon chain comprising 1, 2 or 3 carbon atoms, optionally substituted by an optionally substituted aromatic group, an optionally substituted heterocycle or an amine group belonging to optionally substituted heterocycle;

R16 is a hydrogen atom, halogen or alkoxy group;

R17 is a hydrogen atom, alkoxy group or acetoxy group.

According to one particular embodiment, the group R1 of molecules having formula (I) is selected from the following groups:

a phenyl group, optionally substituted by an F or Cl atom, a methyl or ethyl group, an N,N-dimethyl-sulphonamide or two groups selected from the methyl, ethyl, hydroxy, methoxy or ethoxy groups, a group 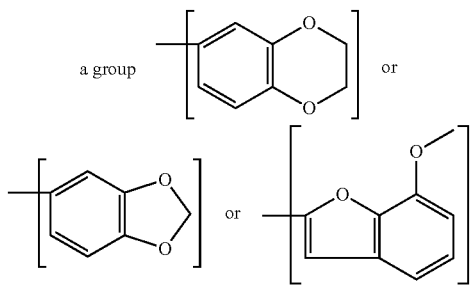

a furan group optionally substituted by a methyl, ethyl, hydroxyl, methoxy or ethoxy group, a thiophene group optionally substituted by a methyl, ethyl, hydroxy, methoxy or ethoxy group;

the group R2 of molecules having formula (I) is selected from the following groups:

a group

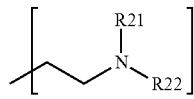

where R21 and R22 are carbon atoms each belonging to an alkyl chain comprising 1, 2 or 3 carbon atoms, or both belonging with the nitrogen atom with which they are bound to the same optionally saturated heterocycle also comprising an oxygen atom or a second nitrogen atom, or a group

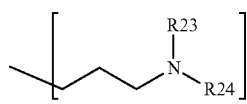

where R23 and R24 are carbon atoms each belonging to an alkyl chain comprising 1, 2 or 3 carbon atoms, or both belonging with the nitrogen atom with which they are bound to the same optionally saturated heterocycle also comprising an oxygen atom or a second nitrogen atom, a or a group

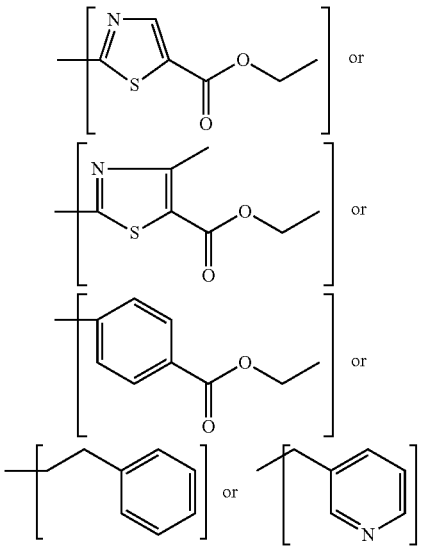

and the group R3 of molecules having formulas (I) is selected from the following groups:
 a non-substituted 2-pyridinyl, 3-pyridinyl or 4-pyridinyl group,
 a phenyl group optionally substituted by a benzoxy group, and/or by a hydroxyl group, and/or by a methyl group, and/or by an ethyl group, and/or by a propyl group, and/or by one or two Br, F or Cl atoms, and/or by one to three hydroxyl, methoxy or ethoxy groups.

According to one particular embodiment, when the group R3 of molecules having formula (I) is a phenyl group, the group R2 of molecules having formula (I) is not an aromatic group or a heterocycle.

According to one particular embodiment, the group R4 of molecules having formula (II) is an optionally saturated carbon chain comprising 1, 2 or 3 carbon atoms; the group R5 is a phenyl group or a secondary amine group substituted by an optionally substituted phenyl group, or by a group

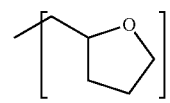

the group R6 of molecules having formula (II) is a hydrogen or chlorine atom or a methyl, ethyl, hydroxyl, methoxy or ethoxy group the group R7 of molecules having formula (II) is a hydrogen or chlorine atom or a methyl, ethyl, hydroxy, methoxy or ethoxy group; and the group R8 of molecules having formula (II) is a hydrogen or chlorine atom or a methyl, ethyl, hydroxy, methoxy or ethoxy group.

According to one particular embodiment,
 the group R9 of molecules having formula (III) is a hydrogen atom and the group R10 is an optionally substituted phenyl group, or the groups R9 and R10 belong to the same optionally substituted heterocycle comprising 2 nitrogen atoms and 4 carbon atoms;
 the group R11 of molecules having formula (III) is a hydrogen atom or methyl, ethyl, hydroxy, methoxy or ethoxy group;

the group R12 of molecules having formula (III) is a hydrogen atom or methyl, ethyl, hydroxy, methoxy or ethoxy group;

the group R13 of molecules having formula (III) is a hydrogen atom or methyl, ethyl, hydroxy, methoxy or ethoxy group;

and the group R14 of molecules having formula (III) is a hydrogen atom or methyl, ethyl, hydroxy, methoxy or ethoxy group.

According to a further particular embodiment, the group R15 of molecules having formula (IV) is a group

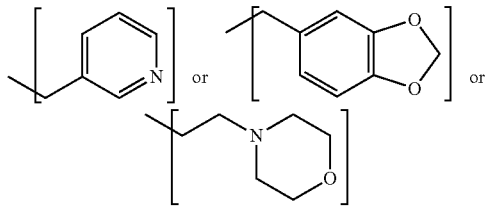

the group R16 of molecules having formula (IV) is a hydrogen or chlorine atom or a methyl, ethyl, hydroxy, methoxy or ethoxy group and the group R17 of molecules having formula (IV) is a methyl, ethyl, hydroxy, methoxy, ethoxy, acetoxy, methoxycarbonyl or ethoxycarbonyl group.

According to one particular embodiment, the molecule according to the invention is not

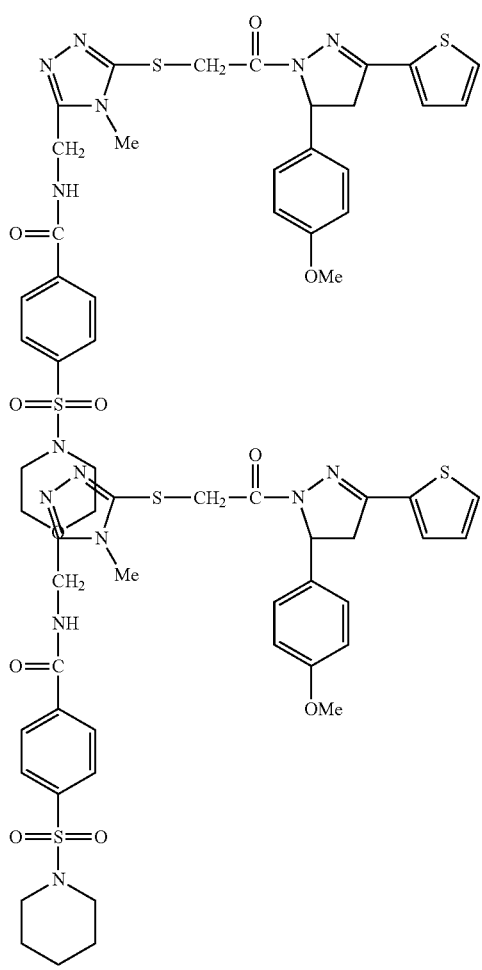

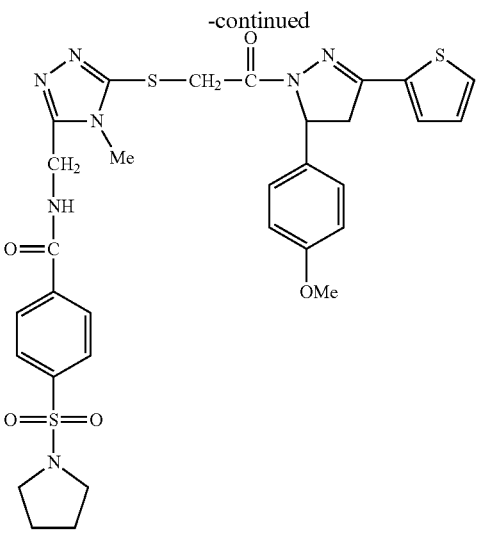

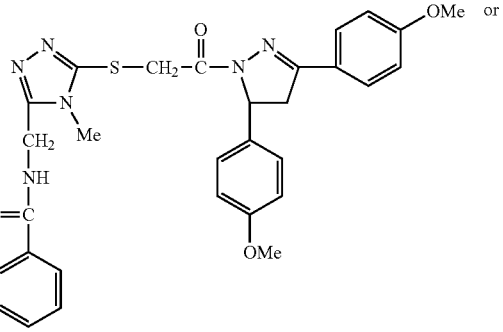

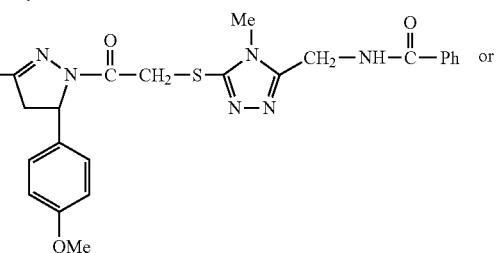

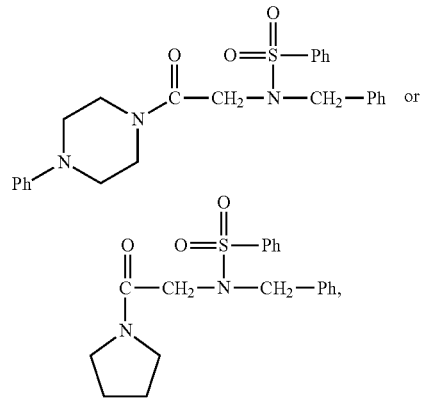

or if it is any of these molecules, it is not used in combination with a glucocorticoid agonist.

The term carbon chain refers to an organic chain having a linear or cyclic, optionally branched, chain formation of adjacent carbon atoms, connected by covalent bonds, as the network thereof. A carbon chain according to the present invention may for example be a linear chain formation of one to twenty, preferably 1 to 12, 1 to 10, 1 to 6, 1 to 5 or 1 to 4 carbon atoms. In particular, it may consist of an alkyl group, i.e. derived from an alkane (linear or branched saturated hydrocarbon molecule) due to the loss of a hydrogen atom, for example a methyl group, an ethyl group, a linear or branched propyl group or a linear or branched butyl group or a linear or branched unsaturated hydrocarbon chain, for example an ethenyl or ethynyl group. It is understood that the electrons of the outer layer (4 in number) of each carbon atom forming the carbon chain network are not involved in a covalent bond with a further carbon atom or with a heteroatom are involved in a covalent bond with a hydrogen atom.

The term heteroatom refers to a non-metallic atom other than carbon or hydrogen, for example oxygen, nitrogen, sulphur, phosphorus or halogens.

The term aromatic or aryl group refers to an unsaturated cycle system observing Hückel's aromaticity rule. For example, it may consist of a phenyl group (group derived from a benzene nucleus).

The term heterocycle refers to a cycle system wherein one or a plurality of carbon atoms is replaced by a heteroatom such as, for example, oxygen, nitrogen or sulphur. It may in particular consist of aromatic heterocycles, such as pyrrole, thiophene, furan and pyridine or of saturated heterocycles, such as sugars, or oses. For example, a heterocycle according to the invention comprises 2 to 8 carbon atoms and 1 to 4 heteroatoms, preferably it comprises 2, 3, 4 or 5 carbon atoms and 1, 2, 3 or 4 heteroatoms.

Each atom belonging to a carbon chain, aromatic group, cycle or heterocycle according to the present invention may be substituted via a covalent bond by one or a plurality of halogens, for example Fluorine, Chlorine, Iodine or Bromine, and/or by one or a plurality of organic groups, for example one or a plurality of aromatic (such as a phenyl group), cyclic, heterocyclic (such as a furan or thiophene group), alkyl (such as a methyl group, ethyl group, linear or branched propyl group or a linear or branched butyl group), alkoxy (such as a methoxy ($OCH_3$) or ethoxy ($OCH_2CH_3$) group), carboxyl (such as a carboxy (COON) group), carbonyl (such as an acetoxy ($OCOCH_3$) or methoxycarbonyl ($COOCH_3$) or ethoxycarbonyl ($COOCH_2CH_3$) group), primary, secondary or tertiary amine, amide (such as an acetamide group) or sulphonamide (such as an N,N-dimethylsulphonamide group) groups. It is understood that a saturated, unsaturated or aromatic cycle or heterocycle may be merged with a further cycle, for example by means of a single or double bond between two carbon atoms.

The present invention also relates to a pharmaceutical composition comprising a molecule according to the invention and a pharmacologically acceptable excipient.

According to one embodiment, the pharmaceutical composition according to the invention also comprises a further therapeutic molecule. For example, it may consist of a therapeutic molecule also used for the prevention or treatment of a condition dependent on a metabolic pathway involving Syk or, on the other hand, a therapeutic molecule used for the prevention or treatment of a condition not dependent on a metabolic pathway involving Syk. According to one particular embodiment, the pharmaceutical composition according to the invention does not comprise a glucocorticoid receptor agonist.

According to a further particular embodiment, the pharmaceutical composition according to the invention may be used in combination with one or a plurality of further pharmaceutical compositions. For example, it may be pharmaceutical compositions also used for the prevention or treatment of a condition dependent on a metabolic pathway involving Syk or, on the other hand, pharmaceutical compositions used for the prevention or treatment of a condition not dependent on a metabolic pathway involving Syk. According to this embodiment, the pharmaceutical composition according to the invention and the further pharmaceutical composition(s) may be administered simultaneously or in alternation, by the same administration route or by different routes. According to one particular embodiment, the pharmaceutical composition according to the invention is not used in combination with a glucocorticoid receptor agonist.

The present invention also relates to a method for identifying an organic molecule having a molecular weight between 50 and 2500 Dalton binding with Syk tyrosine kinase protein and capable of inhibiting by at least 5%, preferably at least 10%, for example at least 15, 20, 25, 30, 35, 40, 45, 50, 55, 60, 65, 70, 75, 80 or 85% in vitro the binding of (i) antibody fragment G4G11 (SEQ ID No. 2), or (ii) antibody fragment G4E4 (SEQ ID No. 3), or (iii) an antibody or antibody fragment which binds with human Syk tyrosine kinase protein on an epitope comprising at least one of residues 65 to 74 of the amino acid sequence of human Syk tyrosine kinase protein represented by the sequence SEQ ID No. 1, or (iv) an antibody or antibody fragment which binds with human Syk tyrosine kinase protein and inhibits by at least 10% the binding of antibody fragments G4G11 or G4E4 with human Syk tyrosine kinase protein (SEQ ID No. 1), to human Syk tyrosine kinase protein or to any of the variants thereof in animals, comprising at least the following steps:

a) screening, from a bank of candidate organic molecules having a molecular weight between 50 and 2500 Da, those liable to bind with Syk protein on the three-dimensional binding cavity on the Syk protein of a molecule selected from the molecules having formula C-13, I, II, III, IV or 1 to 87 as illustrated above;

b) selecting from the molecules identified in a) those capable of inhibiting by at least 5%, preferably at least 10%, for example at least 15, 20, 25, 30, 35, 40, 45, 50, 55, 60, 65, 70, 75, 80 or 85% in vitro the binding of the antibody or antibody fragment (i), (ii), (iii) or (iv) with Syk protein.

According to one particularly preferred embodiment, the molecule from step a) selected from the molecules having formula C-13, I, II, III, IV or 1 to 87 is the molecule C-13, molecule (59) or molecule (51).

According to one preferred embodiment, the method according to the invention comprises an additional step prior to step a) for identifying the three-dimensional binding cavity on the Syk protein of the molecule selected from the molecules having the formula C-13, I, II, III, IV or 1 to 87. This prior step may particularly be performed by means of "in silico docking".

The term "in silico docking" or "molecular docking" or "virtual docking" refers to the use of a bioinformatics tool for predicting and modelling the position of a ligand in a macromolecule. In particular, in silico docking tools can be used to calculate the probability that a given chemical compound will be able to dock with an active target protein, for example on a previously identified three-dimensional binding cavity.

According to one preferred embodiment, the method according to the invention comprises an additional step c) for selecting from the molecules identified in b) those capable of inhibiting by 50% in vitro at mast cell degranulation to a concentration (IC50) between 1 ng/ml and 1 mg/ml, for example at a concentration between 1 ng/ml and 500 µg/ml, between 1 ng/ml and 250 µg/ml, between 1 ng/ml and 100 µg/ml, between 1 ng/ml and 50 µg/ml, between 1 ng/ml and 10 µg/ml, between 1 ng/ml and 5 µg/ml or between 1 ng/ml and 2 µg/ml.

According to one particularly preferred embodiment of the uses and methods described above, the molecule according to the invention is selected from the group consisting of the molecule C-13 and molecules No. 1 to 87 given in table 1.

These molecules were identified by the inventors within the scope of a project following a previous study (Dauvillier et al., 2002[7]), during which they expressed scFv ("single chain variable domain") (or "intracellular antibodies" or "intrabodies"), G4G11 (SEQ ID No. 2) and G4E4 (SEQ ID No. 3) antibody fragments in a mast cell line. This study demonstrated the inhibitory effects of these "intracellular antibodies" or "intrabodies" on the release of allergic mediators induced by FcεRI stimulation on the mast cell membrane. The scFv G4G11 and G4E4 antibody fragments were isolated from a combinatory bank screened against a recombinant protein containing the SH2 domains of Syk and inter-domain A region separating same, i.e. a portion of Syk protein not comprising the Syk kinase domain[8].

The ADA ("antibody displacement assay") method is a method developed by the inventors and described in WO2005106481, particularly for identifying a ligand capable of selectively modulating a functional cascade involving a target, comprising a first step for identifying an intracellular antibody capable of binding with the target and modulating the functional cascade in question, a second step for screening from a bank of small organic molecules, ligands modulating the binding between the target and the intracellular antibody potentially being performed in vitro in an extracellular test, and a third step for identifying from the modulating ligands obtained in step 2, those capable of modulating the functional cascade in the cell.

The inventors suggested the theory whereby the antibody fragments G4G11 and G4E4 bind on a Syk region interacting with one or more essential partners in the functional cascade giving rise to degranulation. Taking into consideration the limits of the use of intracellular antibodies in therapy, such as the effective transfer of the gene encoding the antibody in target cells[9], the inventors sought to isolate organic molecules acting as functional mimics of the intrabody G4G11 and suitable for easier use in therapy. To this end, they used the ADA method for screening a bank of 3000 small organic molecules and identifying potential allergic response inhibitors.

Among the 3000 small organic molecules tested, the inventors identified the small molecule C-13 (methyl 2-{5-[(3-benzyl-4-oxo-2-thioxo-1,3-thiazolidin-5-ylidene)methyl]-2-furyl}benzoate) and demonstrated the ability thereof to modulate the interaction of the antibody fragment G4G11 or G4E4 with Syk in vitro and inhibit mast cell degranulation induced by FcεRI in vitro.

The inventors particularly demonstrated the fact that the compound C-13 inhibits anaphylactic shock when administered orally and has promising anti-allergic properties, illustrating the strong therapeutic potential of medicinal product candidates isolated using the approach described herein.

The inventors also demonstrated the fact that C-13 binds with Syk on a newly identified cavity situated between both SH2 domains and inter-domain A of Syk (FIG. 1). The binding cavity of C-13 forms a unique interaction zone which is specific to Syk, and does not correspond to a known binding side of physiological ligands of Syk such as doubly phosphorylated ITAM peptide on tyrosine residues (FIG. 1A). The results obtained suggest that C-13 Inhibits the interaction of Syk with some of the macromolecular substrates thereof, either directly in that C-13 occupies a surface whereon a partner of Syk could establish direct contact, and/or by means of an allosteric effect.

Figure 3:
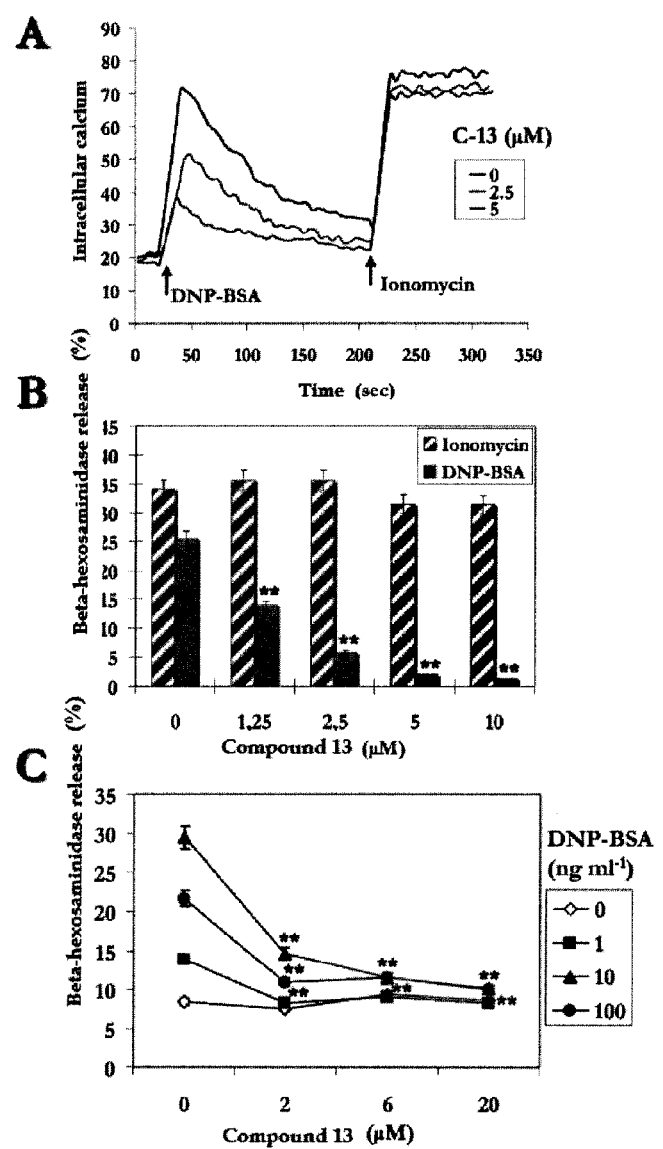
Figure 3:
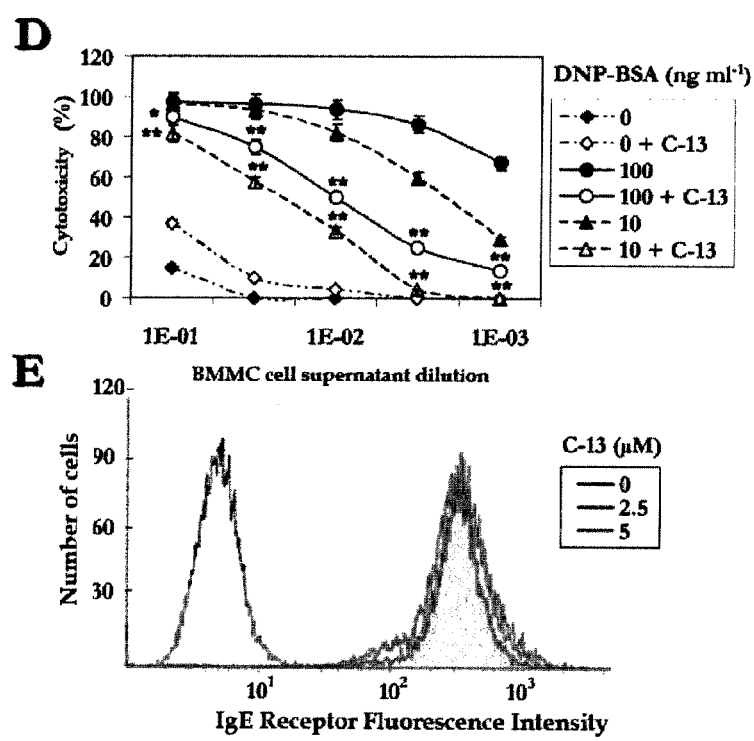

The biochemical studies conducted on mast cells indeed demonstrated that C-13 Inhibits FcεRI-dependent phosphorylation of SLP-76 on tyrosine residues contributing to the adapting function thereof for the binding and/or stabilisation of Btk, PLC-γ and Vav with the macromolecular signalling complex formed with LAT[22, 28-30] (FIG. 2). This affects the phosphorylation and catalytic activity of Btk and PLC-γ renewal in the vicinity of Syk and/or Btk for the complete phosphorylation thereof which is required for maintaining calcium flow and exocytosis[31-35]. Indeed, C-13 inhibited early (β-hexosaminidase release) and delayed (TNF-α secretion) mast cell responses induced by aggregation on the FcεRI receptors with an estimated IC50 of 2 µM (FIG. 3).

Significantly, the oral administration of a single dose of C-13 inhibited IgE-induced passive systemic anaphylaxis (PSA) with an estimated IC50 of 110 mg/kg (FIG. 4), confirming the promising anti-allergic properties of this compound. On the contrary, a single oral administration of 100 mg/kg of C-13 did not affect Syk-dependent neutrophil recruitment induced by thioglycollate in the peritoneal cavity in the presence of *Bordetella pertussis* toxin (FIG. 5A). Furthermore, the inventors demonstrated that, despite the fact that BCR-dependent B lymphocyte in vitro proliferation was inhibited in a dose-dependent fashion by C-13 (FIG. 5B), the antibody responses of mice immunised with a thymus-dependent antigen were not affected by the oral administration of 150 mg/kg of C-13 (FIG. 5C). Therefore, the molecule C-13 does not affect some responses dependent on Syk but not dependent on mast cells in vivo at administration doses and periods at which it is liable to inhibit a severe allergic response.

Taking into consideration the lack of an apparent toxic effect following the oral or local administration of C-13 over a period ranging from one hour to 12 days, C-13 may be considered as the potential first member of a new family of Syk inhibitors suitable for oral administration and pharmacologically active molecules having an anti-inflammatory effect. The pharmaceutical molecule screening approach described herein represents a generic platform wherein the initial use of antibodies makes it possible to detect the domains of the target molecule having a therapeutic potential, thus facilitating the design of chemical molecules (via in silico and/or in vitro screening) capable acting as functional antibody mimics and as potential protein-protein interaction inhibitors. Furthermore, the inventors demonstrated that these small molecules can induce the desired response in cell and animal models, supporting the concept in favour of the replacement of large macromolecules that are difficult to administer by small organic molecules suitable for oral administration.

The possible binding site with Syk was predicted in silico, guided by the location of the epitope of G4G11. One candidate cavity situated next to the epitope of G4G11, on the interface situated between the two SH2 domains and the inter-domain binder of Syk and comprising the residues Ser 9, Gln 43, Phe 51, Ile 66, Glu 67, Arg 68, Glu 69, Leu 70, Asn 71, Gly 72, Thr 73, Tyr 74, Ala 75, Glu 121 and Glu 155 was thus identified (FIG. 1C). Targeted mutagenesis experiments confirmed that the residues Arg 68, Glu 121 and Glu 155 of human Syk protein (SEQ ID No. 1) play a significant role in interaction with C-13, the mutation of said residues suppressing the inhibition caused by C-13, whereas the binding of scFv G4G11 is maintained (FIGS. 1A, 1C). These results tend to confirm the theory whereby the binding cavity of C-13 or Syk is located in the vicinity of the binding site of the intrabody G4G11.

The inventors then performed virtual docking on a molecule bank to identify candidate molecules having the best binding properties on said three-dimension cavity, and tested the ability of said candidate molecules to inhibit the binding of scFv G4G11 with Syk. These molecules are given in table 1 (see example 2). The ability of these molecules to inhibit mast cell degranulation in vitro was also tested. With molecules No. 59 and 61 in particular the concentration inhibiting mast cell degranulation by 50% in vitro is in the region of 5 μM (see FIG. 6).

The results given in the experimental part and particularly in table 1 demonstrate that the molecules or salts according to the invention inhibit type I hypersensitivity reactions, particularly IgE-dependent mast cell degranulation, and are also capable of interfering in vivo with passive cutaneous and systemic anaphylaxis in BALB/c mice.

BRIEF DESCRIPTION OF THE FIGURES

FIG. 1. Binding of C-13 with Syk in vitro. A. Chemical structure of C-13. 3D structure of cavity predicted and validated for C-13 (or "Compound 13") comprising the residues Ser 9, Gln 43, Phe 51, Arg 68, Glu 121 and Glu 155 (mesh representation); the G4G11 epitope comprises the residues 65 to 74 of human Syk protein represented by SEQ ID No. 1. B. Binding of scFv G4G11 fragment with Syk measured using ADA method in the presence of C-13 (■). Binding of C-13 with Syk measured using fluorescence spectroscopy (○) (Kd=4.8±0.2 μM). C. Binding of G4G11 with Syk mutants with ADA method. Significant inhibition with C-13 versus DMF: **P<0.01.

FIG. 2. C-13 inhibits FcεRI-induced mast cell activation. A. The immunoblots produced on RBL-2H3 cell lysates were analysed with immunoblots with the specified antibodies. The in vitro kinase activities of the Syk, Btk and Lyn immunoblots were examined. B. The RBL-2H3 cell lysates and C. BMMCs were subjected to electrophoresis and the proteins were analysed by means of immunoblot. These data are representative of at least two experiments.

FIG. 3. C-13 inhibits FcεRI-dependent calcium release and degranulation. A. FACS analysis of IgE-dependent calcium flow in RBL-2H3 cells. B. Release of β-hexosaminidase in RBL-2H3 cells sensitised with IgE/DNP. C. Release of β-hexosamlnidase and, D. titration of TNF-α in BMMCs cells sensitised with IgE/DNP; C-13: 3 μM. E. FACS analysis of FCεRI surface expression in RBL-2H3 cells. (0=0.25% DMF). Significant inhibition with C-13 versus DMF: **P<0.01 and *P<0.05.

FIG. 4. In vivo studies on BALB/c mice. A-C. PSA response. A. Temperature progression, B. Evans blue extravasation quantification, C Photograph representing Evans blue extravasation according to an oral administration of 130 mg/kg of C-13, a non-relevant compound (IR) or the vector (T); Untreated animal (NT). The ears and tall of the mice received the non-relevant compound (IR) or the vector alone (T) turned a pronounced blue colour, those of the mice treated with C-13 turned a light blue colour and those of the untreated mice are normal in colour D. PCA response: Evans blue extravasation quantification. Significant inhibition with C-13 versus a non-relevant compound: **P<0.01; versus the vehicle+DNP-KLH: *P<0.05.

FIG. 5. In vivo and in vitro effects of C-13 on neutrophils and B lymphocytes. A. Neutrophil recruitment in the peritoneal cavity after injecting thioglycollate or the vehicle in the presence of *Bordetella Pertussis* toxin (where specified) (n=4). B. In vitro B lymphocyte proliferation induced by anti-IgM. C. Serum immunoglobulin concentration 12 days after immunisation with TNP-KLH (n=4).

FIG. 6. Effect of molecules No. 59 (ref. Chembridge 7501888) and 61 (ref. Chembridge 7722851) on RBL-2H3 cell degranulation. The level of β-hexosaminidase release in RBL-2H3 cells sensitised with IgE/DNP was measured in the presence A. of molecule No. 59 and B. of Molecule No. 61 at concentrations ranging from 0 to 40 μM.

FIG. 7. Amino acid sequences of intrabodies scFv A. G4G11 (SEQ ID No. 2) and B. G4E4 (SEQ ID No. 3).

FIG. 8. Amino acid sequence of human A. (SEQ ID No. 1) corresponding to accession No. NP_003168 (NCBI) and B. murine Syk protein corresponding to accession No. NP_035648 (NCBI). The residues identified as belonging to the three-dimensional binding cavity of C-13 on human Syk protein (A) and the equivalent thereof on murine Syk protein (B) are shown in bold type and underlined.

FIG. 9. Schematic representation of the metabolic pathways involving Syk tyrosine kinase in mast cells.

FIG. 10. Toxicity test of C-13 on BMMC cells. The BMMC cells were incubated at 37° C. in the presence of 2.5 μM or 5 μM of C-13, 0.25% DMF or Staurosporine. The percentages of live BMMC cells after 3 hours and after 5 days were detected by means of double Annexin-V and Propidium Iodide labelling. The viability of BMMC cells incubated in the presence of 2.5 μM or 5 μM of C-13 or 0.25% DMF was not affected to noteworthy degree after 3 hours (78%, 74% and 79% respectively) or five days (62, 56 and 57%, respectively). On the other hand, the viability of BMMC cells treated under the same conditions with Staurosporine was reduced to a level of 16% after only 3 hours.

EXAMPLES

Example 1

Identification of Molecule C-13 Potentially Suitable for Oral Administration to Prevent Anaphylactic Shock 1) Identification of Compound 13 (C-13) and the Binding Cavity Thereof on Syk The inventors developed the ADA (Antigen Displacement Assay) method to identify small molecules capable of displacing the association with scFv G4G11 with Syk. Of the members of a bank of 3000 chemical molecules, 15 small molecules proved to be capable of competing with the binding of scFv G4G11 with Syk, and of these compounds, that hereinafter referred to as C-13 (FIG. 1A) displayed the best inhibition potential with an estimated IC50 of 4 μM (FIG. 1B). This result is in line with the dissociation constant value (or Kd) equal to 4.8 μM obtained by measuring by means of fluorescence spectroscopy (or spectrofluorometry) the in vitro affinity of C-13 for Syk (FIG. 1B). To understand the mode of action of C-13, the inventors firstly identified the binding site of G4G11 using the SPOT method[16]. An epitope located on the N-terminal SH2 domain of Syk, comprising amino acids 65-74 and 100% preserved in mouse, rat and human sequences, was identified.

On the basis of this information and the known 3D structure of the peptide complex formed by the SH2 domains of Syk and ITAM motifs[17], the inventors used computing approaches to locate a putative binding site for C-13. A candidate cavity comprising the residues Ser 9, Gln 43, Phe 51, Ile 66, Glu 67, Arg 68, Glu 69, Leu 70, Asn 71, Gly 72, Thr 73, Tyr 74, Ala 75, Glu 121 and Glu 155 of human Syk protein (see FIG. 8A, SEQ ID No. 1) and situated in the vicinity of the G4G11 epitope was identified (FIG. 1C). A structural analysis specified that the residues Ser 9, Gln 43, Phe 51, Arg 68, Glu 121 and Glu 155 could be involved in the binding of the ligand, and could be mutated without impairing the 3D structure of the protein. To validate the cavity in more detail, these six amino acids were mutated individually and the Syk mutants were subjected to the ADA test. The residues Arg 68, Glu 121 and Glu 155 proved to have a significant role in the interaction with the small molecule, given that the mutation thereof cancelled the inhibition caused by C-13, whereas the binding of scFv G4G11 was maintained (FIG. 1C). These data confirmed the fact that the binding cavity of C-13 on Syk is located in the vicinity of the binding site of G4G11.

2) FcεRI-Induced Mast Cell Activation

To examine the functional similarities with G4G11, the inventors explored the biological effects of C-13 on mast cell activation. The incubation of RBL-2H3 cells with C-13 did not affect the phosphorylation and FcεRI-induced kinase activity of Syk (FIG. 2A) and, accordingly, the overall level of tyrosine phosphorylation of all the cell proteins known as being essentially Syk-dependent was normal (FIGS. 2B, C). Similarly to the intrabody G4G11, C-13 inhibited the phosphorylation and FcεRI-induced kinase activity of Btk (FIG. 2A) and the phosphorylation of PLC-γ1 and PLC-γ2, the two PLC-γ isoforms expressed in mast cells (FIGS. 2A, C). PTK Lyn phosphorylates both Syk and Btk giving rise to the complete activation thereof and the subsequent phosphorylation of PLC-γ[18]. Given that C-13 did not affect FcεRI-dependent Lyn activation (FIG. 2A), it can be concluded that the reduction of the level of Btk and PLC-γ phosphorylation could be due to a defect with respect to the correct location thereof in the vicinity of the upstream PTK.

3) Fyn- and Lyn-Dependent Signalling Cascade Analysis

In mast cells, the signalling cascade Fyn/Gab2/PI3K gives rise to the activation of PI3K and the generation of PI-3,4,5-P3 recruiting a number of proteins containing a pleckstrin homology domain (PH), including Btk and PLC-γ on the plasma membrane[19]. The analysis of the phosphorylation of Akt, a PI3K activity marker, indicated that C-13 did not affect the Fyn-dependent cascade (FIGS. 2B, C), suggesting that the reduced level of phosphorylation of Btk and PLC-γ was not due to a defect on the membrane location thereof, known as being an essential factor in the increase in calcium flows[20].

Btk and PLC-γ recruitment on the membrane also requires the canonical signalling cascade Lyn/Syk/LAT/SLP-76. The phosphorylation of LAT by Syk gives rise to the translocation of SLP-76 to the complex organised by LAT[21], where SLP-76 is co-located with Syk[22]. This location enables Syk to phosphorylate N-terminal tyrosines of SLP-76[23] which become binding sites for Vav, Nck and Btk. LAT and SLP-76 (via the proline-rich domain thereof recruiting PLC-γ) interact to locate PLC-γ on said membrane complex, enabling the phosphorylation and activation of PLC-γ by Btk[24] and/or Syk[25]. The use of phospho-specific antibodies demonstrated that C-13 inhibits the phosphorylation of SLP-76, but increases the phosphorylation of LAT in a dose-dependent fashion (FIG. 2A). The inventors suggested the theory whereby the inhibition of SLP-76 phosphorylation could enable a larger quantity of LAT to interact with Syk, thus causing an increase in the phosphorylation level thereof. These results demonstrate that the reduction in SLP-76 phosphorylation was not due to a defect in terms of the recruitment thereof to LAT, and resulted in a co-location defect of Btk and, to a lesser extent, that of Vav with SLP-76 (FIG. 2A). Nevertheless, Vav phosphorylation known to be independent from the recruitment thereof to SLP-76[28] was not inhibited (FIG. 2A).

4) MAPK Activation

The association of SLP-76 with Vav and/or Nck plays a role in optimal MAP kinase activation in mast cells[27]. The inventors demonstrated that C-13 affects MAP kinase activation slightly (evaluated via the phosphorylation level thereof): a high C-13 concentration reduces the phosphorylation level ERK1/2, whereas the phosphorylation levels of p38 and JNK remain normal (FIGS. 2B, C).

5) Calcium Flow and Degranulation

Figure 10:
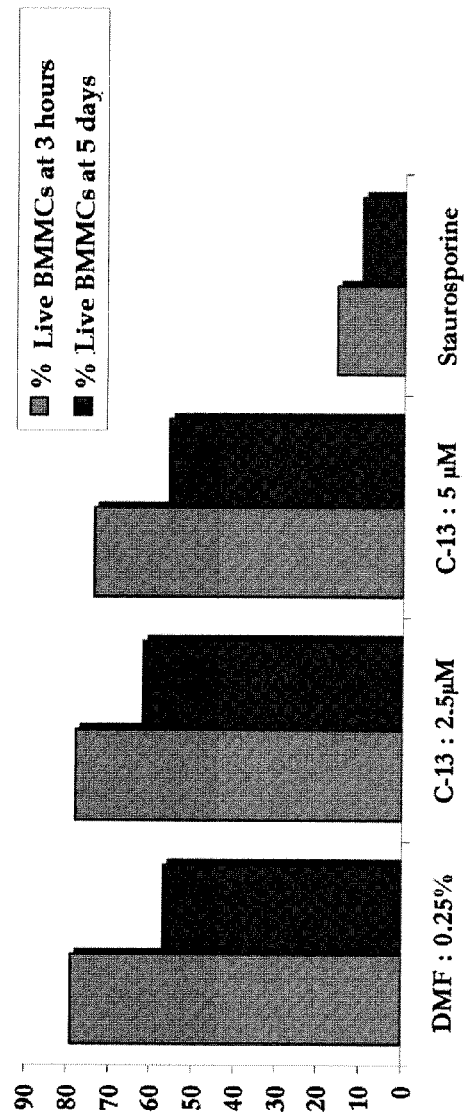

Binding of Btk and Vav with SLP-76 is critical for regulating PLC-γ activity on the membrane, calcium mobilisation and granule exocytosis[27, 28]. The inventors demonstrated that the association of PLC-γ with LAT was inhibited by C-13 in a dose-dependent fashion (FIG. 2A). Consistently with the defect in terms of PLC-γ1 and PLC-γ2 phosphorylation, the mast cells showed a reduced calcium flow range in response to FcεRI binding (FIG. 3A), and early and delayed FcεRI-induced allergic responses in BMMC ("bone marrow derived mast cell") cells and in the RBL-2H3 cell line are also weakened in a dose-dependent fashion, based on the measurement of β-hexosaminidase release and TNF-α secretion (FIGS. 3B, C, D). The results also demonstrated that C-13 had no toxic effect on mast cells. Indeed, ionomycin-induced degranulation (FIG. 3B), or BMMC cell viability (see FIG. 10) were not detectably affected by treatment with C-13. Furthermore, the defects observed in terms of mast cell activation are not due to a reduced level of FcεRI surface expression, flow cytometry analysis indicating that the cells incubated with C-13 express similar levels of FcεRI to those of control cells (FIG. 3E).

6) Passive Systemic (PSA) and Cutaneous Anaphylaxis (PCA)

Finally, to extend these observations to mast cell functions in vivo, the inventors tested the effects of C-13 on passive systemic (PSA) and cutaneous anaphylaxis (PCA) induced in BALB/c mice by administering DNP-specific IgE molecules followed by intravenous stimulation with DNP-KLH hapten. This mimics systemic anaphylaxis as demonstrated by the immediate cardiopulmonary changes and the increase in vascular permeability. The intensity of systemic anaphylaxis was determined by measuring both the drop in body temperature and the increase in vascular permeability following antigen administration. After the oral administration of C-13 (and prior to antigen stimulation), the animals appeared to be healthy with no obvious sign of toxicity. The administration of a single oral dose of 100 mg/kg of C-13 inhibited hypothermia and accelerated the recovery of the animals (FIG. 4A). On the basis of the Evans blue extravasation quantification, it was determined that C-13 inhibits the increase in vascular permeability with an estimated IC50 of 110 mg/kg (FIGS. 4B and 4C). C-13 also demonstrated an inhibitory effect on PCA with an estimated IC50 of 25 μm (FIG. 4D).

Example 2

Identification Using Binding Cavity of C-13 of Further Potential Mast Cell Degranulation Inhibitors Using the binding cavity identified in example 1-1), virtual docking screening was conducted on a set of 350,000 molecules contained in the ChemBridge Corporation (San Diego, USA) chemical bank to identify the 1000 molecules displaying the best binding properties in said cavity.

The ADA method was then applied to each of these 1000 molecules to measure the ability thereof to inhibit the binding of scFv G4G11 with Syk. The 87 molecules having the best inhibition rate (between 11 and 86.5%) are given in table 1.

Figure 6:
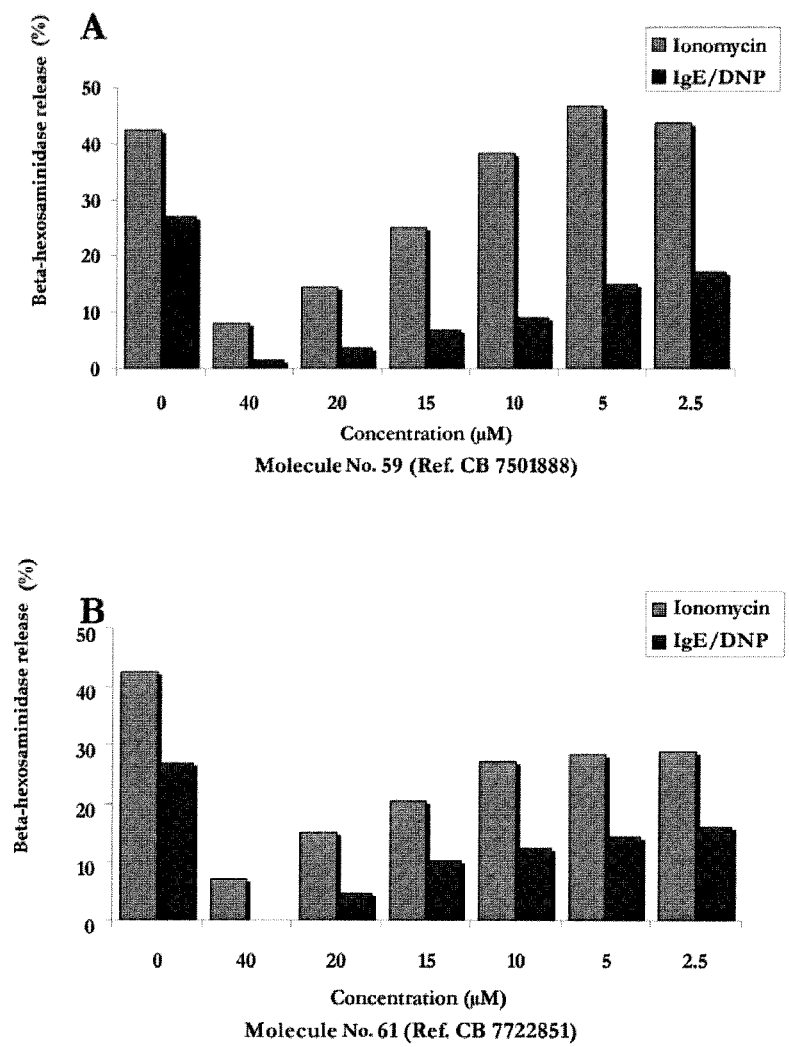

These 87 molecules were also tested in vitro to assess the ability thereof to inhibit RBL-2H3 cell degranulation (see table 1). The two molecules exhibiting the best potential (molecules No. 59 and 61) were tested at various concentrations on RBL-2H3 cells to assess the concentration inhibiting degranulation by 50% in more detail (see FIG. 6).

Finally, the in vitro affinity of the molecule C-13 and some of the 87 molecules mentioned above for Syk protein was measured by means of fluorescence spectroscopy (or spectrofluorometry) and is expressed by the dissociation constant (or Kd) in µmole/liter (µM).

TABLE 1

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{23}H_{17}NO_4S_2$ | 6197026 | methyl 2-{5-[(3-benzyl-4-oxo-2-thioxo-1,3-thiazolidin-5-ylidene)methyl]-2-furyl} benzoate | — | 81% | 1 µg/ml | 4.8 µM | C-13 | — |
| $C_{29}H_{21}ClN_2O_4$ | 6752784 | 4-(4-chloro benzoyl)-3-hydroxy-5-(3-phenoxy phenyl)-1-(3-pyridinyl methyl)-1,5-dihydro-2H-pyrrol-2-one | 611 | 86.5 | >10 µg/ml | 5 µM | 1 | I |
| $C_{23}H_{23}N_3O_5S$ | 6670340 | 5-(2,4-dimethoxy phenyl)-3-hydroxy-1-[3-(1H-imidazol-1-yl)propyl]-4-(2-thienyl carbonyl)-1,5-dihydro-2H-pyrrol-2-one | 792 | 81 | >10 µg/ml | 16.3 µM | 2 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{24}H_{20}BrNO_6$ | 6422575 | {4-bromo-2-[3-(ethoxy carbonyl)-2-methyl-5-oxo-4,5-dihydro-1H-indeno[1,2-b]pyridin-4-yl]phenoxy} acetic acid | 706 | 81 | >10 µg/ml | 6.2 µM | 3 | — |
| $C_{26}H_{30}N_2O_5$ | 6882059 | 3-hydroxy-5-(3-methoxy phenyl)-4-(4-methyl benzoyl)-1-[3-(4-morpholinyl) propyl]-1,5-dihydro-2H-pyrrol-2-one | 243 | 79.5 | >10 µg/ml | 9.4 µM | 4 | I |
| $C_{25}H_{25}N_3O_5$ | 7111786 | 4-benzoyl-5-(2,5-dimethoxy phenyl)-3-hydroxy-1-[3-(1H-imidazol-1-yl)propyl]-1,5-dihydro-2H-pyrrol-2-one | 557 | 77.5 | >10 µg/ml | — | 5 | I |
| $C_{28}H_{25}NO_7$ | 6203863 | ethyl 4-[3-benzoyl-2-(2,4-dimethoxy phenyl)-4-hydroxy-5-oxo-2,5-dihydro-1H-pyrrol-1-yl] benzoate | 423 | 73.5 | >10 µg/ml | 6.1 µM | 6 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{26}H_{30}N_2O_5$ | 7347627 | 4-(2,5-dimethyl benzoyl)-3-hydroxy-5-(2-methoxy phenyl)-1-[2-(4-morpholinyl) ethyl]-1,5-dihydro-2H-pyrrol-2-one | 775 | 72 | >10 µg/ml | — | 7 | I |
| $C_{24}H_{20}BrNO_5S$ | 7489416 | 5-(3-bromo-4-hydroxy-5-methoxy phenyl)-3-hydroxy-1-(2-phenylethyl)-4-(2-thienyl carbonyl)-1,5-dihydro-2H-pyrrol-2-one | 648 | 71 | >10 µg/ml | — | 8 | I |
| $C_{29}H_{21}FN_2O_4$ | 6719738 | 4-(4-fluoro benzoyl)-3-hydroxy-5-(3-phenoxy phenyl)-1-(3-pyridinyl methyl)-1,5-dihydro-2H-pyrrol-2-one | 977 | 71 | >10 µg/ml | — | 9 | I |
| $C_{25}H_{21}FN_2O_5S$ | 6650234 | ethyl 2-[3-(4-fluorobenzoyl)-4-hydroxy-2-(4-methyl phenyl)-5-oxo-2,5-dihydro-1H-pyrrol-1-yl]-4-methyl-1,3-thiazole-5-carboxylate | 946 | 71 | ~10 µg/ml | 6.3 µM | 10 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| C<sub>26</sub>H<sub>24</sub>N<sub>2</sub>O<sub>5</sub> | 6652639 | 5-(2,5-dimethoxy phenyl)-3-hydroxy-4-(4-methyl benzoyl)-1-(3-pyridinyl methyl)-1,5-dihydro-2H-pyrrol-2-one | 829 | 70.5 | >10 µg/ml | — | 11 | I |
| C<sub>25</sub>H<sub>22</sub>N<sub>2</sub>O<sub>6</sub>S | 6673225 | ethyl 2-[3-benzoyl-4-hydroxy-2-(4-methoxy phenyl)-5-oxo-2,5-dihydro-1H-pyrrol-1-yl]-4-methyl-1,3-thiazole-5-carboxylate | 301 | 69 | >10 µg/ml | — | 12 | I |
| C<sub>29</sub>H<sub>25</sub>NO<sub>5</sub> | 6800873 | 3-[2-(2,4-dimethoxy phenyl)-2-oxoethyl]-3-hydroxy-1-(1-naphthyl methyl)-1,3-dihydro-2H-indol-2-one | 250 | 67.5 | >10 µg/ml | 4.6 µM | 13 | — |
| C<sub>24</sub>H<sub>27</sub>N<sub>3</sub>O<sub>5</sub> | 6879058 | 3-hydroxy-4-(4-methoxy-2-methyl benzoyl)-1-[2-(4-morpholinyl) ethyl]-5-(3-pyridinyl)-1,5-dihydro-2H-pyrrol-2-one | 758 | 67.5 | >10 µg/ml | — | 14 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{25}H_{22}N_4O_3S$ | 6282824 | 2-methoxy-N-(4-(4-methyl-5-[(2-oxo-2-phenylethyl)thio]-4H-1,2,4-triazol-3-yl)phenyl)benzamide | 905 | 67.5 | ~2.5 µg/ml | 5.6 µM | 15 | II |
| $C_{24}H_{20}N_2O_5S$ | 6750319 | methyl 2-[3-benzoyl-4-hydroxy-2-(4-methylphenyl)-5-oxo-2,5-dihydro-1H-pyrrol-1-yl]-4-methyl-1,3-thiazole-5-carboxylate | 850 | 67 | >10 µg/ml | — | 16 | I |
| $C_{28}H_{32}N_2O_2$ | 6474819 | 4-[(4-benzyl-1-piperidinyl)methyl]-N-(2-methoxy-5-methylphenyl)benzamide | 954 | 63 | >10 µg/ml | 17.9 µM | 17 | — |
| $C_{24}H_{25}N_3O_5S$ | 6498669 | 4-{[N-[(4-methoxyphenyl)sulphonyl]-N-(2-phenylethyl)glycyl]amino}benzamide | 808 | 63 | >10 µg/ml | 0.8 µM | 18 | III |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{27}H_{31}FN_2O_4$ | 6651552 | 4-(4-fluoro benzoyl)-3-hydroxy-5-(4-isopropyl phenyl)-1-[3-(4-morpholinyl) propyl]-1,5-dihydro-2H-pyrrol-2-one | 100 | 60 | >10 µg/ml | — | 19 | I |
| $C_{28}H_{26}N_2O_4$ | 6453860 | N,N'-1,5-naphthaene-diylbis[2-(3-methyl phenoxy) acetamide] | 145 | 60 | >10 µg/ml | — | 20 | — |
| $C_{23}H_{23}N_3O_6S$ | 6853966 | N-[4-({[4-(acetyl amino) phenyl] sulphonyl} amino)-2,5-dimethoxy phenyl] benzamide | 11 | 58 | >10 µg/ml | — | 21 | — |
| $C_{28}H_{37}N_3O_3$ | 6866968 | 7,7-dimethyl-1-(4-methyl phenyl)-2,5-dioxo-N-(2,2,6,6-tetramethyl-4-piperidinyl)-1,2,5,6,7,8-hexahydro-3-quinoline carboxamide | 255 | 57.5 | >10 µg/ml | — | 22 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| C$_{25}$H$_{23}$N$_3$O$_3$S | 7938324 | 4-(benzyl{[1-phenyl-3-(2-thienyl)-1H-pyrazol-4-yl]methyl}amino)-4-oxo butanoic acid | 795 | 57 | >10 µg/ml | — | 23 | — |
| C$_{25}$H$_{27}$FN$_2$O$_5$ | 6905988 | 4-(4-fluoro benzoyl)-3-hydroxy-5-(3-methoxy phenyl)-1-[3-(4-morpholinyl) propyl]-1,5-dihydro-2H-pyrrol-2-one | 843 | 57 | >10 µg/ml | — | 24 | I |
| C$_{27}$H$_{31}$ClN$_2$O$_7$ | 6885782 | 4-(4-chloro benzoyl)-3-hydroxy-1-[3-(4-morpholinyl) propyl]-5-(3,4,5-trimethoxy phenyl)-1,5-dihydro-2H-pyrrol-2-one | 249 | 56.5 | >10 µg/ml | — | 25 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{26}H_{30}N_2O_4$ | 6663684 | 4-benzoyl-3-hydroxy-5-(4-isopropyl phenyl)-1-[2-(4-morphopinyl) ethyl]-1,5-dihydro-2H-pyrrol-2-one | 530 | 56.5 | >10 μg/ml | — | 26 | I |
| $C_{25}H_{27}ClN_2O_6$ | 6672500 | 4-(4-chloro benzoyl)-5-(3,4-dimethoxy phenyl)-3-hydroxy-1-[2-(4-morpholinyl) ethyl]-1,5-dihydro-2H-pyrrol-2-one | 194 | 55 | >10 μg/ml | — | 27 | I |
| $C_{28}H_{32}N_2O_5$ | 7721949 | 1-[2-(diethyl amino)ethyl]-5-(2,5-dimethoxy phenyl)-3-hydroxy-4-(4-methyl benzoyl)-1,5-dihydro-2H-pyrrol-2-one | 139 | 54 | >10 μg/ml | — | 28 | I |
| $C_{25}H_{19}FN_6O_2S$ | 7966545 | 2-fluoro-N-[(5-{[(4-oxo-3,4-dihydro-2-quinazolinyl) methyl]thio}-4-phenyl-4H-1,2,4-triazol-3-yl)methyl] benzamide | 773 | 53.5 | ~10 μg/ml | 6.7 μM | 29 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{25}H_{27}N_3O_5S$ | 7437580 | 2-{[4-(1,3-dioxo-1,3-dihydro-2H-isoindol-2-yl)butanoyl]amino}-N-(tetrahydro-2-furanyl methyl)-5,6-dihydro-4H-cyclopenta[b]thiophene-3-carboxamide | 222 | 51 | >10 µg/ml | — | 30 | — |
| $C_{25}H_{27}FN_2O_6$ | 6654239 | 5-(3,4-dimethoxy phenyl)-4-(4-fluoro benzoyl)-3-hydroxy-1-(2-(4-morpholinyl)ethyl]-1,5-dihydro-2H-pyrrol-2-one | 343 | 50 | >10 µg/ml | — | 31 | I |
| $C_{25}H_{29}N_3O_6S$ | 6670570 | 4-({4-hydroxy-1-[2-(4-morpholinyl)ethyl]-5-oxo-2-phenyl-2,5-dihydro-1H-pyrrol-3-yl}carbonyl)-N,N-dimethyl benzene sulphonamide | 926 | 50 | >10 µg/ml | — | 32 | I |
| $C_{25}H_{28}N_2O_6$ | 6670673 | 5-(2,4-dimethoxy pheny)-4-(4-fluorobenzoyl)-3-hydroxy-1-[2-(4-morpholinyl)ethly]-1,5-dihydro-2H-pyrrol-2-one | 742 | 50 | >10 µg/ml | — | 33 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{25}H_{28}N_2O_5$ | 6670747 | 3-hydroxy-5-(4-methoxyphenyl)-4-(4-methylbenzoyl)-1-(2-(4-morpholinyl)ethyl]-1,5-dihydro-2H-pyrrol-2-one | 413 | 50 | >10 µg/ml | — | 34 | I |
| $C_{23}H_{26}N_2O_7$ | 6671401 | 5-(3,4-dimethoxyphenyl)-4-(2-furoyl)-3-hydroxy-1-[2-(4-morpholinyl)ethyl]-1,5-dihydro-2H-pyrrol-2-one | 954 | 50 | >10 µg/ml | — | 35 | I |
| $C_{25}H_{27}ClN_2O_6$ | 6672500 | 4-(4-chlorobenzoyl)-5-(3,4-dimethoxyphenyl)-3-hydroxy-1-[2-(4-morpholinyl)ethyl]-1,5-dihydro-2H-pyrrol-2-one | 194 | 50 | >10 µg/ml | — | 36 | I |
| $C_{25}H_{22}N_2O_6S$ | 6673225 | ethyl 2-[3-benzoyl-4-hydroxy-2-(4-methoxyphenyl)-5-oxo-2,5-dihydro-1H-pyrrol-1-yl]-4-methyl-1,3-thiazole-5-carboxylate | 124 | 50 | >10 µg/ml | — | 37 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{23}H_{26}N_2O_6S$ | 6677533 | 5-(3,4-dimethoxy phenyl)-3-hydroxy-1-[2-(4-morpholinyl)ethyl]-4-(2-thienyl carbonyl)-1,5-dihydro-2H-pyrrol-2-one | 409 | 50 | >10 µg/ml | — | 38 | I |
| $C_{24}H_{25}ClN_2O_5$ | 6683618 | 4-(4-chloro benzoyl)-3-hydroxy-5-(4-methoxy phenyl)-1-[2-(4-morpholinyl)ethyl]-1,5-dihydro-2H-pyrrol-2-one | 808 | 50 | >10 µg/ml | — | 39 | I |
| $C_{27}H_{31}N_3O_3S$ | 6417902 | N-[2-(4-benzyl-1-piperazinyl)-2-oxoethyl]-N-(3,5-dimethyl phenyl)benzene sulphonamide | 897 | 49.5 | >10 µg/ml | — | 40 | III |
| $C_{26}H_{20}ClNO_5$ | 6437157 | 1-methyl-2-(4-methyl phenyl)-2-oxoethyl 2-(3-chloro-4-methyl phenyl)-1,3-dioxo-5-isoindoline carboxylate | 871 | 49.5 | >10 µg/ml | — | 41 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{25}H_{28}N_2O_6S$ | 6465972 | N~2~-[(3,4-dimethoxy phenyl) sulphonyl]-N~1~-(2-methoxy-5-methylphenyl-N~2~-(4-methylphenyl) glycinamide | 926 | 49 | >10 μg/ml | — | 42 | III |
| $C_{26}H_{29}FN_2O_6$ | 7723671 | 5-(2,5-dimethoxy phenyl)-4-(4-fluoro benzoyl)-3-hydroxy-1-[3-(4-morpholinyl) propyl]-1,5-dihydro-2H-pyrrol-2-one | 34 | 48.5 | >10 μg/ml | — | 43 | I |
| $C_{24}H_{24}ClFN_2O_4$ | 6648368 | 4-(4-chlorobenzoyl)-5-(2-fluorophenyl)-3-hydroxy-1-[3-(4-morpholinyl) propyl]-1,5-dihydro-2H-pyrrol-2-one | 465 | 48.5 | >10 μg/ml | — | 44 | I |
| $C_{26}H_{29}FN_2O_4$ | 6656195 | 4-(4-fluoro benzoyl)-3-hydroxy-5-(4-isopropyl phenyl)-1-[2-(4-morpholinyl) ethyl]-1,5-dihydro-2H-pyrrol-2-one | 613 | 48.5 | >10 μg/ml | — | 45 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{23}H_{30}N_4O_5S$ | 7778331 | 4-{[2-(4-morpholinyl) ethyl]amino}-3-(4-morpholinyl sulphonyl)-N-phenylbenzamide | 998 | 48 | >10 µg/ml | 3 µM | 46 | — |
| $C_{23}H_{24}ClN_5O_3S$ | 6994060 | 2-chloro-N-{4-[4-methyl-5-({2-oxo-2-[(tetrahydro-2-furanyl methyl) amino] ethyl}thio)-4H-1,2,4-triazol-3-yl]phenyl} benzamide | 623 | 47.5 | >10 µg/ml | — | 47 | II |
| $C_{28}H_{33}N_3O_3S$ | 6458830 | N-[2-(4-benzyl-1-piperazinyl)-2-oxoethyl]-N-(3,4-dimethyl phenyl)-4-methyl benzene sulphonamide | 837 | 47 | >10 µg/ml | — | 48 | III |
| $C_{26}H_{26}N_2O_5$ | 7524107 | 2-[(4-{[(4-isopropyl phenoxy) acetyl]amino}-3-methyl benzoyl) amino] benzoic acid | 789 | 46.5 | ~10 µg/ml | 5.5 µM | 49 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{24}H_{27}Cl_2N_3O_5S$ | 6661524 | 4-({2-(3,4-dichloro phenyl)-1-[3-(dimethyl amino)propyl]-4-hydroxy-5-oxo-2,5-dihydro-1H-pyrrol-3-yl} carbonyl)-N,N-dimethyl benzene sulphonamide | 428 | 46.5 | >10 μg/ml | — | 50 | I |
| $C_{24}H_{27}N_3O_5$ | 7739436 | 4-(1,3-benzodioxol-5-yl carbonyl)-1-[3-(diethyl amino)propyl]-3-hydroxy-5-(3-pyridinyl)-1,5-dihydro-2H-pyrrol-2-one | 976 | 46 | >10 μg/ml | — | 51 | I |
| $C_{23}H_{28}N_2O_7$ | 6881804 | 1-[2-(dimethyl amino)ethyl]-3-hydroxy-4-(5-methyl-2-furoyl)-5-(3,4,5-trimethoxy phenyl)-1,5-dihydro-2H-pyrrol-2-one | 230 | 46 | >10 μg/ml | — | 52 | I |
| $C_{23}H_{26}N_2O_6$ | 6907921 | 3-hydroxy-5-(3-methoxy phenyl)-4-(5-methyl-2-furoyl)-1-[2-(4-morpholinyl)ethyl]-1,5-dihydro-2H-pyrrol-2-one | 609 | 45.5 | >10 μg/ml | — | 53 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{22}H_{18}N_4O_5S$ | 7495334 | ethyl 4-({[(5,6-di-2-furyl-1,2,4-triazin-3-yl)thio]acetyl}amino)benzoate | 380 | 43 | ~5 µg/ml | 1.6 µM | 54 | — |
| $C_{28}H_{25}N_3O_5S$ | 7509862 | ethyl 5-cyano-4-(2-furyl)-6-({2-[(3-methoxyphenyl)amino]-2-oxoethyl}thio)-2-phenyl-1,4-dihydro-3-pyridine carboxylate | 170 | 42.5 | ~5 µg/ml | — | 55 | — |
| $C_{28}H_{34}N_2O_6$ | 7325385 | 5-(2,3-dimethoxyphenyl)-4-(2,5-dimethylbenzoyl)-3-hydroxy-1-[3-(4-morpholinyl)propyl]-1,5-dihydro-2H-pyrrol-2-one | 65 | 42 | ~10 µg/ml | — | 56 | I |
| $C_{24}H_{16}N_4O_4$ | 6669449 | 3-(6-amino-5-cyano-3-phenyl-1,4-dihydropyrano[2,3-c]pyrazol-4-yl)phenyl 2-furoate | 140 | 42 | >10 µg/ml | — | 57 | — |
| $C_{25}H_{34}N_2O_4$ | 7348779 | 1,4-bis[(mesityloxy)acetyl]piperazine | 209 | 40 | ~10 µg/ml | — | 58 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{27}H_{27}ClN_4O_4S$ | 7501888 | N-(4-chloro phenyl)-2-{[4-(2-phenyl ethyl)-5-(3,4,5-trimethoxy phenyl)-4H-1,2,4-triazol-3-yl]thio} acetamide | 544 | 40 | ~2 µg/ml | 8.2 µM | 59 | — |
| $C_{26}H_{20}O_6$ | 6946138 | {[3-(ethoxy carbonyl)-2-phenyl-1-benzofuran-5-yl]oxy} (phenyl) acetic acid | 298 | 40 | >10 µg/ml | — | 60 | — |
| $C_{26}H_{23}ClN_4O_4S$ | 7722851 | ethyl 4-({[1-(4-chloro phenyl)-5-oxo-3-(3-pyridinyl methyl)-2-thioxo-4-imidazolidinyl] acetyl} amino) benzoate | 638 | 39.5 | ~2 µg/ml | 21.8 µM | 61 | IV |
| $C_{26}H_{24}N_2O_7$ | 7517583 | 5,5'-oxybis [2-(tetrahydro-2-furanyl methyl)-1H-isoindole-1,3(2H)-dione] | 912 | 38.5 | >10 µg/ml | — | 62 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{26}H_{22}N_4O_3S$ | 6634701 | 7-acetyl-6-[3-(benzyloxy)phenyl]-3-(methylthio)-6,7-dihydro[1,2,4]triazino[5,6-d][3,1]benzoxazepine | 934 | 38.5 | ~5 µg/ml | — | 63 | — |
| $C_{25}H_{22}N_4O_5$ | 7726450 | 3-hydroxy-1-imidazol-1-[3-(1H-imidazol-1-yl)propyl]-4-[(7-methoxy-1-benzofuran-2-yl)carbonyl]-5-(2-pyridinyl)-1,5-dihydro-2H-pyrrol-2-one | 472 | 37.5 | >10 µg/ml | — | 64 | I |
| $C_{25}H_{30}N_4O_6S$ | 6662088 | 4-{[4-hydroxy-1-[3-(4-morpholinyl)propyl]-5-oxo-2-(3-pyridinyl)-2,5-dihydro-1H-pyrrol-3-yl]carbonyl}-N,N-dimethylbenzenesulphonamide | 158 | 37 | >10 µg/ml | — | 65 | I |
| $C_{23}H_{25}N_5O_3S$ | 7752193 | N-{1-[4-allyl-5-({2-[(3-methoxyphenyl)amino]-2-oxoethyl}thio)-4H-1,2,4-triazol-3-yl]ethyl}benzamide | 248 | 35 | ~5 µg/ml | 8 µM | 66 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{25}H_{26}N_4O_4S$ | 7238569 | N-(2-hydroxy-1,1-dimethylethyl)-5-{4-[(3-hydroxy phenyl) amino]-1-phthalazinyl}-2-methyl benzene sulphonamide | 749 | 32 | >10 μg/ml | — | 67 | — |
| $C_{25}H_{25}FN_2O_6$ | 7724000 | 4-(1,3-benzodioxol-5-ylcarbonyl)-5-(2-fluorophenyl)-3-hydroxy-1-[3-(4-morpholinyl) propyl]-1,5-dihydro-2H-pyrrol-2-one | 303 | 30 | ~10 μg/ml | — | 68 | I |
| $C_{23}H_{21}N_3O_5S$ | 7443270 | N-(2,4-dimethoxy-phenyl)-2-{[3-(2-furylmethyl)-4-oxo-3,4-dihydro-2-quinazolinyl]thio} acetamide | 895 | 30 | ~5 μg/ml | — | 69 | — |
| $C_{26}H_{24}N_2O_4$ | 7245019 | N-[(2-hydroxy-7-methyl-3-quinolinyl) methyl]-3-methoxy-N-(2-methoxy phenyl) benzamide | 608 | 30 | >10 μg/ml | — | 70 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{24}H_{25}ClN_2O_5$ | 6909597 | 4-(4-chlorobenzoyl)-3-hydroxy-5-(3-methoxyphenyl)-1-[2-(4-morpholinyl)ethyl]-1,5-dihydro-2H-pyrrol-2-one | 790 | 29 | >10 µg/ml | — | 71 | I |
| $C_{26}H_{25}N_3O_4$ | 7661882 | 2-(4-methoxyphenoxy)-N-[2-methyl-5-(3-methyl-4-oxo-3,4-dihydro-1-phthalazinyl)benzyl]acetamide | 941 | 28 | ~10 µg/ml | — | 72 | — |
| $C_{25}H_{26}N_2O_5$ | 7667791 | N-{4-[({[4-(4-methoxyphenyl)tetrahydro-2H-pyran-4-yl]methyl}amino)carbonyl]phenyl}-2-furamide | 797 | 28 | >10 µg/ml | — | 73 | — |
| $C_{26}H_{30}N_2O_6$ | 6891745 | 4-benzoyl-5-(2,3-dimethoxyphenyl)-3-hydroxy-1-(3-(4-morpholinyl)propyl]-1,5-dihydro-2H-pyrrol-2-one | 115 | 27.5 | >10 µg/ml | — | 74 | I |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{26}H_{29}N_5O_4S$ | 7783660 | isopropyl 3-({[(4-allyl-5-{[(3-methyl benzoyl) amino] methyl}-4H-1,2,4-triazol-3-yl)thio]acetyl} amino) benzoate | 266 | 27 | ~5 µg/ml | 4.8 µM | 75 | II |
| $C_{24}H_{30}N_5O_3$ | 7653478 | 2-{5-[1-(4-morpholinyl) cyclohexyl]-1H-tetrazol-1-yl}ethyl 1-naphthyl carbamate | 365 | 27 | >10 µg/ml | — | 76 | — |
| $C_{26}H_{23}N_3O_7$ | 7723330 | methyl 4-({[3-(1,3-benzodioxol-5-ylmethyl)-2,5-dioxo-1-phenyl-4-imidazol idinyl]acetyl} amino) benzoate | 965 | 26 | >10 µg/ml | — | 77 | IV |
| $C_{28}H_{29}N_3O_2$ | 7199725 | 4-(3,4-dihydro-2(1H)-isoquinolinyl-methyl)-N-[2-(1-pyrrolidinyl carbonyl) phenyl] benzamide | 987 | 25 | >10 µg/ml | — | 78 | — |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| C₂₉H₃₀ClNO₃ | 6987235 | 9-{3-chloro-4-[(4-methyl benzyl)oxy] phenyl}-10-ethyl-3,4,6,7,9,10-hexahydro-1,8(2H,5H)-acridine diane | 680 | 25 | >10 µg/ml | — | 79 | — |
| C₂₅H₃₂N₂O₅S | 7140931 | ethyl 1-(4-{[(3,4-dimethyl phenyl)(methyl sulphonyl) amino] methyl} benzoyl)-4-piperidine carboxylate | 14 | 24.5 | >10 µg/ml | — | 80 | — |
| C₂₃H₂₂N₂O₆S | 7787455 | methyl 4-{[N-(3-methoxy phenyl)-N-(phenyl sulphonyl) glycyl]amino} benzoate | 407 | 20 | >10 µg/ml | — | 81 | III |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| 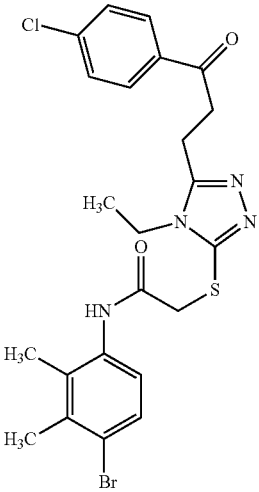<br>$C_{22}H_{23}BrClN_5O_2S$ | 7660465 | N-{[5-({2-[(4-bromo-2,3-dimethyl phenyl) amino]-2-oxoethyl} thio)-4-ethyl-4H-1,2,4-triazol-3-yl]methyl}-4-chloro benzamide | 881 | 20 | ~7 µg/ml | 3.2 µM | 82 | II |
| 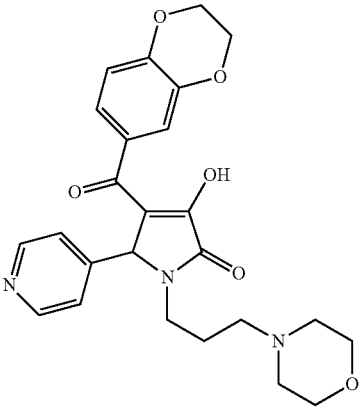<br>$C_{25}H_{27}N_3O_6$ | 7661751 | 4-(2,3-dihydro-1,4-benzodioxin-6-ylcarbonyl)-3-hydroxy-1-[3-(4-morpholinyl) propyl]-5-(4-pyridinyl)-1,5-dihydro-2H-pyrrol-2-one | 951 | 19 | ~10 µg/ml | — | 83 | I |
| 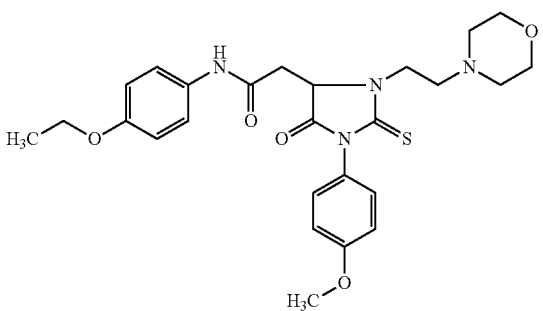<br>$C_{26}H_{32}N_4O_5S$ | 7722914 | N-(4-ethoxy phenyl)-2-{1-(4-methoxy phenyl)-3-[2-(4-morpholinyl) ethyl]-5-oxo-2-thioxo-4-imidazol idinyl}acetamide | 806 | 19 | ~7 µg/ml | 15.6 µM | 84 | IV |

TABLE 1-continued

C-13 and the 87 molecules identified using C-13 and the antibody fragment G4G11

| Structure | CB ref. | Name | Rank | In vit. inhib. | Degran. IC50 | Kd | No. | Gp |
|---|---|---|---|---|---|---|---|---|
| $C_{26}H_{25}BrN_2O_6$ | 7745040 | 5-(3-bromo phenyl)-3-hydroxy-4-[(7-methoxy-1-benzofuran-2-yl) carbonyl]-1-[2-(4-morpholinyl) ethyl]-1,5-dihydro-2H-pyrrol-2-one | 313 | 18 | ~10 µg/ml | — | 85 | I |
| $C_{26}H_{29}N_3O_5$ | 7735385 | 1-[3-(diethyl amino)propyl]-3-hydroxy-4-[(7-methoxy-1-benzofuran-2-yl) carbonyl]-5-(2-pyridinyl)-1,5-dihydro-2H-pyrrol-2-one | 21 | 17 | ~10 µg/ml | — | 86 | I |
| $C_{27}H_{28}N_6OS$ | 7756003 | 1-(4-{[(4,6-dimethyl-2-pyrimidinyl) thio]acetyl}-1-piperazinyl)-4-(4-methyl phenyl) phthalazine | 361 | 11 | ~5 µg/ml | — | 87 | — |

CB ref: ChemBridge reference;
Rank: rank of each molecule in the list of the 1000 best molecules after in silico docking;
In vit. inhib.: mean inhibition % obtained with each molecule for the displacement of the binding of scFv G4G11 with Syk in vitro in the ADA method;
Degran. IC50: concentration inhibiting mast cell degranulation by 50%;
Kd: dissociation constant with respect to Syk measured in vitro by spectrofluorometry
No.: number assigned by the inventors;
Gp: groups to which the molecules belong.

Example 3

Materials and Methods

1) Chemical products and antibodies. A chemical bank of 3000 molecules (a varied subset) was acquired from ChemBridge, Inc. (San Diego, Calif.). Stocks of solutions of small molecules were prepared at a rate of 10 mM in DMSO (dimethylsulphoxide), except for C-13 (methyl 2-{5-[(3-benzyl-4-oxo-2-thioxo-1,3-thiazolidin-5-ylidene)methyl]-2-furyl}benzoate, ChemBridge ID No. 6197026) prepared in DMF (dimethylformamide). Unless specified otherwise, all the reagents were supplied by Sigma. Dinitrophenyl (DNP) hapten was acquired from Calbiochem. Sepharose GammaBind G and all the secondary antibodies were supplied by GE Health Amersham Biosciences. The anti-Syk, anti-Lyn, anti-Btk, anti-PLC-γ1, anti-PLC-γ2, anti-LAT, anti-SLP-76, anti-p38, anti-JNK, anti-Vav, anti-Akt1 and 9E10 antibodies conjugated with HRP were acquired from Santa Cruz Biotechnology. The anti-phospho-p44/42 MAP Kinase, anti-p44/42 MAP Kinase, anti-phospho-p38, anti-phospho-JNK, anti-phospho-Akt1 antibodies were acquired from Cell Signaling. The anti-phospho-LAT and anti-phospho-PLC-γ1 antibodies were supplied by Biosource and the anti-phospho-SLP-76 antibodies by BD Pharmingen. The 4G10 anti-phosphotyrosine monoclonal antibody was acquired from Upstate Biotechnology.

2) ADA method: ELISA type high-speed molecule screening test, based on antibody displacement (WO 2005106481).

The recombinant fusion protein GST:Syk 6-242[8] comprising the residues 6 to 242 of murine Syk tyrosine kinase protein illustrated in FIG. 8B (SEQ ID No. 4) was immobilised on an ELISA plate at a final concentration of 10 μg ml$^{-1}$. For the screening of the chemical molecule bank, the small molecules, diluted in PBS at a final concentration of 10 μM were added to the wells for one hour at ambient temperature, before adding the fragment scFv G4G11 at a final concentration of 100 nM for an additional hour. The binding of G4G11 with Syk was assessed by adding the 9E10 monoclonal antibody conjugated with HRP detecting the amino acid sequence EQKLISEEDLN of human c-myc protein located at the C-terminal end of the scFv fragment. To generate Syk mutants, targeted mutagenesis was used on GST:Syk 6-242 protein and the binding of G4G11 with the mutants was assessed in the presence of 5 μM of C-13.

3) Cells, culture conditions and functional tests. Anti-DNP 2682-I mouse monoclonal antibody was used as the culture supernatant of hybridomas containing 1 μg/ml of IgE. Femoral bone marrow cells were sampled and cultured in Opti-MEM medium (Gibco) supplemented with 10% foetal calf serum and 4% X63 transfectant supernatant secreting murine IL-3. RBL-2H3 (ATCC) leukaemic rat basophil cells were maintained in a single-layer culture in RPMI 1640 medium supplemented with 10% foetal calf serum (Gibco). Measurements of β-hexosaminidase released by the RBL-2H3 cells were performed as described previously[7], except that, after 12-16 hours of incubation with anti-DNP IgE (0.5 μg/ml), the cells were incubated for 90 min at 37° C. in RPMI medium supplemented with the specified concentrations of C-13 or DMF (0.25%). The cells were stimulated for 45 min with DNP-BSA (50 ng ml$^{-1}$) or ionomycin (1.5 μM). The BMMC cells were incubated for one hour at 37° C. with anti-DNP IgE (100 ng/ml). They were then incubated with C-13 (3 μM) or DMF (0.3%) for 3 hours at 37° C., and stimulated with varied concentrations of DNP-BSA. The level of β-hexosaminidase released was measured 10 min later and the TNF-α titration was performed by means of a cytotoxicity test on L929 cells as described previously[10], 3 hours after stimulation. The results illustrated in FIG. 3 are representative of three independent experiments.

4) Immunoprecipitations, in vitro kinase assays and immunodetection. All the experiments were conducted as described previously[7], except that, before stimulation with DNP-BSA (50 ng ml$^{-1}$, 3 min), the RBL-2H3 cells were incubated for 90 min at 37° C. in RPMI medium supplemented with the specified concentrations of C-13 or DMF. The cells were solubilised in DOC modified lysis buffer (1% NP-40, 0.25% sodium deoxycholate, 0.1% SDS in PBS butter supplemented with protease and phosphatase inhibitors) and the protein concentration was determined (BCA Protein Assay, PIERCE). For immunoprecipitations, cell lysates, non-stimulated and stimulated with IgE/DNP were incubated with preformed complexes of antibodies and Sepharose GammaBind G, and the in vitro kinase activity of Syk, Btk and Lyn immunoprecipitates were examined. Before SDS-PAGE gel separation the lysates or immunoprecipitates were prepared by adding SDS sample buffer (60 mM Tris, pH 6.8, 2.3% SDS, 10% glycerol, 0.01% bromophenol blue). The proteins were transferred onto a nitrocellulose membrane (Schleicher & Schuell), and detected using suitable antibodies and the chemoluminescence system improved (Exacta-Cruz, Santa Cruz Biotechnology).

5) Flow cytometry analysis of level and calcium mobilisation and FcεRI membrane expression. The intracellular free calcium concentration was determined by previously charging 1×10$_5$ cells with 5 mM of Fluo-3 AM (Molecular Probes, Invitrogen) in the presence of 0.2% Pluronic F-127 for 30 min at ambient temperature. Prior to stimulation with DNP-BSA or ionomycin, the cells were treated for 90 min at 37° C. in RPMI medium supplemented with C-13 or DMF (0.25%), and the intracellular free calcium concentration was measured with a flow cytometer (Beckton Dickinson). For the FcεRI surface expression evaluation, the cells were incubated for 2 hours at 37° C. with anti-DNP IgE. Membrane-bound IgE was detected using biotinylated anti-mouse Ig, and streptavidine conjugated with Fitc.

Figure 4:
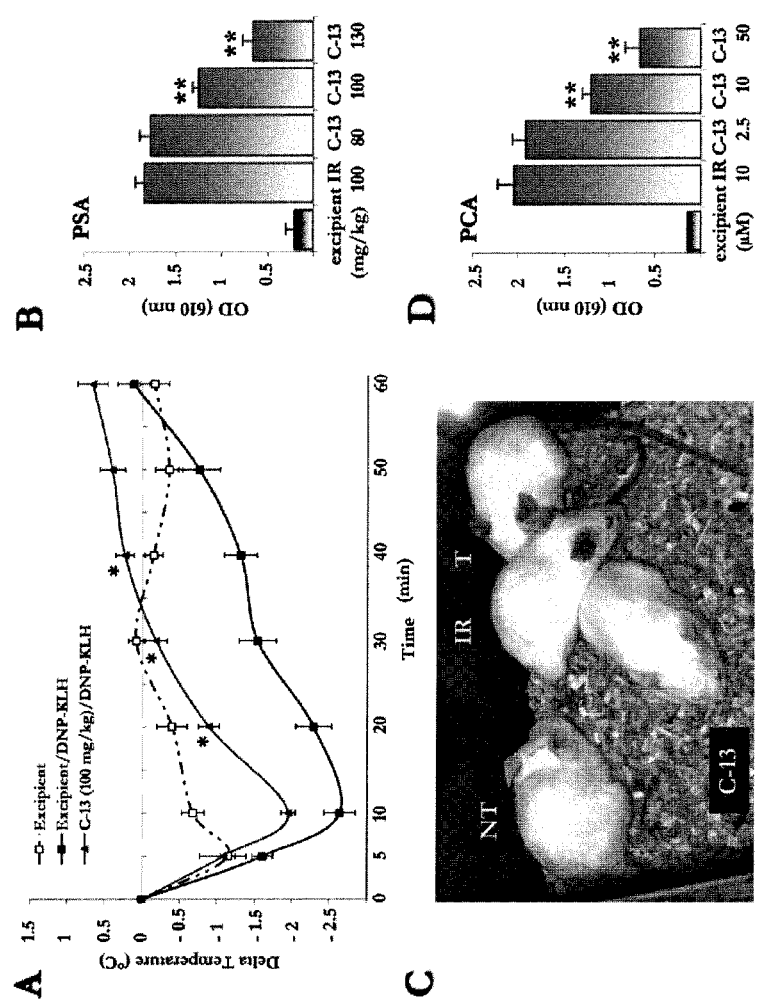

6) Anaphylaxis induction. Female BALB/c mice (aged 6-8 weeks) were acquired from Charles River and kept at the IRCM animal house under pathogen-free conditions. The Ig-dependent passive systemic anaphylaxis (PSA) and passive cutaneous anaphylaxis (PCA) protocols were conducted as described previously[11]. Briefly, the mice received, by intravenous injection, 100 μg of IgE (SPE-7, Sigma) in 200 μl of PBS for PSA, or, by intradermal injection, 25 ng of IgE in 10 μl of PBS for PCA, and were stimulated 24 hours later by means of an intravenous injection of 1 mg of DNP-KLH in 2% of Evans blue. C-13, a non-relevant chemical molecule or the vehicle were administered 1 hours before stimulation, either orally (PSA) in 200 μl of 1% carboxymethylcellulose, or locally in the ear by moans of intradermal injection (PCA) in an acetone/olive oil mixture (4:1). The animals were sacrificed 20 min after stimulation. The ears were removed, ground and Evans blue was extracted after overnight incubation in formamide at 80° C. For the temperature measurements in PSA, C-13 (100 mg/kg) or the vehicle were administered orally, 3 hours prior to stimulation performed in the absence of Evans blue. The temperature was measured using an electronic thermometer with a rectal probe (YSI, Yellow Springs, Ohio) before stimulation and for 60 minutes afterwards, prior to sacrifice. The absorbance was measured at 610 nm. The experiments were conducted with 4-5 mice per condition. The data illustrated in FIG. 4 are representative of three different experiments.

7) Structural studies. The three-dimensional cavities liable to be pharmaceutical targets were predicted using Q-SiteFinder[12] and ICM[13]. The molecule C-13 was docked using LigandFit[14] and Surflex[15]. The first 20 positions were analysed and a consensus position is given in FIG. 1A. The images were generated with PyMol.

Figure 5:
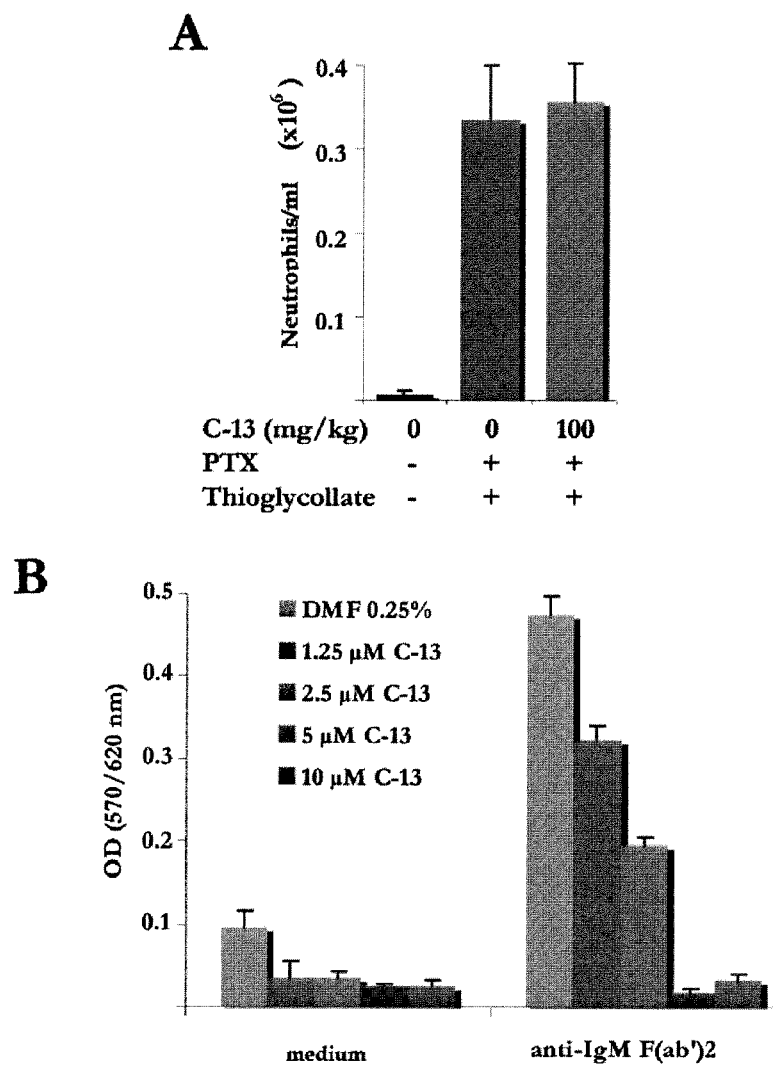
Figure 5:
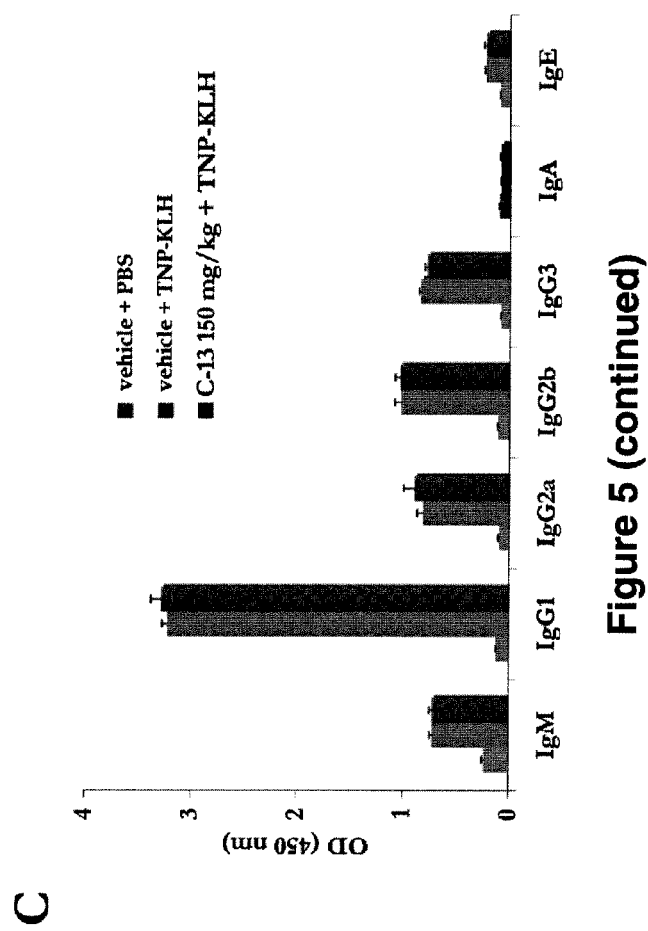

8) Peritonitis (FIG. 5). Syk-dependent peritoneal neutrophil recruitment was induced in 8-week old female BALB/c mice as described in[36] by intravenous injection of 4 μg of *Bordetella pertussis* toxin (donated by Dr D. Raze, Inserm, Lille, France) and 2 hours later by intraperitoneal injection of 4% thioglycollate in sterile water. A peritoneal lavage was performed with 5 ml of PBS 4 hours later and the total number of neutrophils was determined after labelling with anti-Gr1 conjugated with APC (Becton-Dickinson) and flow cytometry analysis. C-13 (100 mg/kg) in CMC or the vehicle alone was administered orally one hour prior to injecting *Bordetella pertussis* toxin.

9) In vitro B Lymphocyte purification and proliferation. Spleen B lymphocyte cells were purified from 8-week old female BALB/c mice on magnetic beads by negative selection using micro-beads coated with CD43 and LS columns (Miltenyi Biotec) as described previously[37].

After two hours of incubation with variable concentrations of C-13 or the vehicle, 50,000 cells were cultured for 48 hours in 96-well plates in the presence of absence of 10 µg/ml of donkey anti-mouse IgM F(ab')$_2$ fragment (Jacson Immunoresearch). Alamar blue (Serotec) was added to the cultures 24 prior to measuring the reduced versus oxidised forms of the reagent at 570 and 620 nm, in accordance with the manufacturer's instructions.

10) Antibody production (FIG. 5C). This experiment was conducted as described in[38]. Eight-week old female BALB/c mice received an oral dose of C-13 (150 mg/kg) in 1% CMC or the vehicle alone, were immunised 3 hours later by an intraperitoneal injection of 10 µg of trinitophenyl-keyhole limpet haemocyanin (TNP-KLH) in Rehydragel alum (Reheiss). The serum was collected before immunisation and on day 12. The antigen-specific immunoglobulin levels were measured by means of ELISA with 10 µg/ml of plate-bound TNP-OVA (Biosearch technologies) as the capture agent. The IgM, IgG1, IgG2a, IgG2b, IgG3 and IgA levels were measured using samples diluted to 1:5000 using goat antibodies conjugated with peroxidase and isotype-specific (Southern Biotechnology), whereas the IgE levels were measured using samples diluted to 1:50 using biotinylated anti-mouse IgE rat antibodies (Becton Dickinson) and streptavidine conjugated with peroxidase (R&D Systems). After incubation with TMB substrate, the optical density (OD) was measured at 450 nm.

11) Statistical analyses. The mean numeric data are expressed as means±standard deviations (SD). Student's t test was used to determine the statistical significance of the differences between groups.

12) C-13 toxicity test on BMMC cells. To assess the potential toxic effect of C-13 on mast cells, BMMC cells were incubated for 5 days at 37° C. in the presence of 2.5 µM or 5 µM of C-13, or 0.25% DMF (corresponding to the DMF concentration used with 5 µM of C-13) under the same conditions as for functional tests. Double labelling with Annexin-V and Propidium Iodide demonstrated the level of BMMC cell viability after 3 hours and after 5 days. The viability of the BMMC cells treated under the same conditions with Staurosporine was measured under the same conditions.

REFERENCES

1. Kambayashi T, Koretzky G A. Proximal signaling events in Fc epsilon RI-mediated mast cell activation. J Allergy Clin Immunol 2007; 119:544-52; quiz 53-4.
2. Rivera J, Gilfillan A M. Molecular regulation of mast cell activation. J Allergy Clin Immunol 2006; 117:1214-25; quiz 26.
3. Costello P S, Turner M, Walters A E, Cunningham C N, Bauer P H, Downward J, et al. Critical role for the tyrosine kinase Syk in signalling through the high affinity IgE receptor of mast cells. Oncogene 1996; 13:2595-605.
4. Wong W S, Leong K P. Tyrosine kinase inhibitors: a new approach for asthma. Biochim Biophys Acta 2004; 1897:53-69.
5. Turner M, Schweighoffer E, Colucci F, Di Santo J P, Tybulewicz V L. Tyrosine kinase Syk: essential functions for immunoreceptor signalling. Immunol Today 2000; 21:148-54.
6. Coopman P J, Mueller S C. The Syk tyrosine kinase: a new negative regulator in tumor growth and progression. Cancer Lett 2006; 241:159-73,
7. Dauvillier S, Merida P, Visintin M, Cattaneo A, Bonnerot C, Dariavach P. Intracellular single-chain variable fragments directed to the Src homology 2 domains of Syk partially inhibit Fc epsilon RI signaling in the RBL-2H3 cell line. J Immunol 2002; 169:2274-83.
8. Peneff C, Lefranc M P, Dariavach P. Characterisation and specificity of two single-chain Fv antibodies directed to the protein tyrosine kinase Syk. J Immunol Methods 2000; 236:105-15.
9. Lobato M N, Rabbitts T H. Intracellular antibodies and challenges facing their use as therapeutic agents. Trends Mol Med 2003; 9:390-8.
10. Latour S, Bonnerot C, Fridman W H, Daeron M. Induction of tumor necrosis factor-alpha production by mast cells via Fc gamma R. Role of the Fc gamma RIII gamma subunit. J Immunol 1992; 149:2155-62.
11. Dombrowicz D, Flamand V, Miyajima I, Ravetch J V, Galli S J, Kinet J P. Absence of Fc epsilonRI alpha chain results in upregulation of Fc gammaRIII-dependent mast cell degranulation and anaphylaxis. Evidence of competition between Fc epsilonRI and Fc gammaRIII for limiting amounts of FcR beta and gamma chains. J Clin Invest 1997; 99:915-25.
12. Laurie A T, Jackson R M. Q-SiteFinder: an energy-based method for the prediction of protein-ligand binding sites. Bioinformatics 2005; 21:1908-16.
13. An J, Totrov M, Abagyan R. Comprehensive identification of "druggable" protein ligand binding sites. Genome Inform 2004; 15:31-41.
14. Venkatachalam C M, Jiang X, Oldfield T, Waldman M. LigandFit: a novel method for the shape-directed rapid docking of ligands to protein active sites. J Mol Graph Model 2003; 21:289-307.
15. Jain A N. Surflex: fully automatic flexible molecular docking using a molecular similarity-based search engine. J Med Chem 2003; 46:499-511.
16. Frank R, Overwin H. SPOT synthesis. Epitope analysis with arrays of synthetic peptides prepared on cellulose membranes. Methods Mol Biol 1996; 66:149-69.
17. Futterer K, Wong J, Grucza R A, Chan A C, Waksman G. Structural basis for Syk tyrosine kinase ubiquity in signal transduction pathways revealed by the crystal structure of its regulatory SH2 domains bound to a dually phosphorylated ITAM peptide. J Mol Biol 1998; 281:523-37.
18. Nadler M J, Matthews S A, Turner H, Kinet J P. Signal transduction by the high-affinity immunoglobulin E receptor Fc epsilon RI: coupling form to function. Adv Immunol 2000; 76:325-55.
19. Parravicini V. Gadina M, Kovarova M, Odom S. Gonzalez-Espinosa C, Furumoto Y, et al. Fyn kinase initiates complementary signals required for IgE-dependent mast cell degranulation. Nat Immunol 2002; 3:741-8.
20. Rameh L E, Rhee S G, Spokes K, Kazlauskas A, Cantley L C, Cantley L G. Phosphoinositide 3-kinase regulates phospholipase Cgamma-mediated calcium signaling. J Biol Chem 1998; 273:23750-7.
21. Saitoh S, Odom S, Gomez G, Sommers C L, Young H A, Rivera J, et al. The four distal tyrosines are required for LAT-dependent signaling in FcepsilonRI-mediated mast cell activation. J Exp Med 2003; 190:831-43.
22. Silverman M A, Shoag J, Wu J, Koretzky G A. Disruption of SLP-76 interaction with Gads inhibits dynamic clustering of SLP-76 and FcepsilonRI signaling in mast cells. Mol Cell Biol 2006; 26:1826-38.
23. Hendricks-Taylor L R, Motto DG, Zhang J, Siraganian R P, Koretzky GA. SLP-76 is a substrate of the high affinity IgE receptor-stimulated protein tyrosine kinases in rat basophilic leukemia cells. J Biol Chem 1997; 272: 1363-7.
24. Takata M. Kurosaki T. A role for Bruton's tyrosine kinase in B cell antigen receptor-mediated activation of phospholipase C-gamma 2, J Exp Med 1996; 184:31-40.
25. Law C L, Chandran K A, Sidorenko S P, Clark E A. Phospholipase C-gamma1 interacts with conserved phosphotyrosyl residues in the linker region of Syk and is a substrate for Syk. Mol Cell Biol 1996; 16:1305-15.
26. Pivniouk V I, Martin T R, Lu-Kuo JM, Katz H R, Oettgen H C, Geha R S. SLP-76 deficiency impairs signaling via the high-affinity IgE receptor In mast cells. J Clin Invest 1999; 103:1737-43.
27. Kettner A, Pivniouk V, Kumar L, Falet H, Lee J S, Mulligan R, et al. Structural requirements of SLP-76 in signaling via the high-affinity immunoglobulin E receptor (Fc epsilon RI) in mast cells. Mol Cell Biol 2003; 23:2395-406.
28. Manetz T S, Gonzalez-Espinosa C, Arudchandran R, Xirasagar S, Tybulewicz V, Rivera J. Vav1 regulates phospholipase cgamma activation and calcium responses in mast cells. Mol Cell Biol 2001; 21:3763-74.
29. Wilson B S, Pfeiffer J R, Oliver J M. FcepsilonRI signaling observed from the inside of the mast cell membrane. Mol Immunol 2002; 38:1259-68.
30. Wu J N, Jordan M S, Silverman M A, Peterson E J, Koretzky G A. Differential requirement for adapter proteins Src homology 2 domain-containing leukocyte phosphoprotein of 76 kDa and adhesion- and degranulation-promoting adapter protein in FcepsilonRI signaling and mast cell function. J Immunol 2004; 172:6768-74.
31. Barker S A, Caldwell K K, Pfeiffer J R, Wilson B S. Wortmannin-sensitive phosphorylation, translocation, and activation of PLCgamma1, but not PLCgamma2, in antigen-stimulated RBL-2H3 mast cells. Mol Biol Cell 1998; 9:483-96.
32. Flucklger A C, Li Z, Kato R M, Wahl M I, Ochs H D, Longnecker R, et al. Btk/Tec kinases regulate sustained increases in intracellular Ca2+ following B-cell receptor activation. Embo J 1998; 17:1973-85.
33. Scharenberg A M, El-Hillal O, Fruman D A, Beitz L O, Li Z, Lin S, et al. Phosphatidylinositol-3,4,5-trisphosphate (PtdIns-3,4,5-P3)/Tec kinase-dependent calcium signaling pathway: a target for SHIP-mediated inhibitory signals. Embo J 1998; 17:1961-72.
34, Wen R, Jou S T, Chen Y, Hoffmeyer A, Wang D. Phospholipase C gamma 2 is essential for specific functions of Fc epsilon R and Fc gamma R. J Immunol 2002; 169:6743-52.
35. Qi Q, August A. Keeping the (Kinase) Party Going: SLP-78 and ITK Dance to the Beat. Sci STKE 2007; 2007:pe39.
36, Mocsai A, Thou M, Meng F, Tybulewicz V L, Lowell C A. Syk is required for integrin signaling in neutrophils. Immunity 2002; 16: 547-558.
37. Matsumoto T, Guo Y J, Ikejima T, Yamada H. Induction of cell cycle regulatory proteins by murine B cell proliferating pectic polysaccharide from the roots of *Bupleurum falcatum* L. Immunology letters 2003; 89: 111-118.
38. Okkenhaug K, Bilancio A, Farjot G, Priddle H, Sancho S, Peskett E, et al. Impaired B and T cell antigen receptor signaling in p110delta PI 3-kinase mutant mice. Science 2002; 297: 1031-1034.
39. Gell P G H, Coombs R R A, eds. Clinical Aspects of Immunology. 1st ed. Oxford, England: Blackwell; 1963
40. S. M. Berge et al. Pharmaceutical Salts, J. Pharm. Sci, 1977, 66:p. 1-19

---

The invention claimed is:

1. A method for treating a type I hypersensitivity reaction or an autoimmune disease dependent on metabolic pathways involving spleen tyrosine kinase (Syk) in a human, which comprises administering a compound to the human, wherein said compound is
   (a) compound C-13 having the following formula

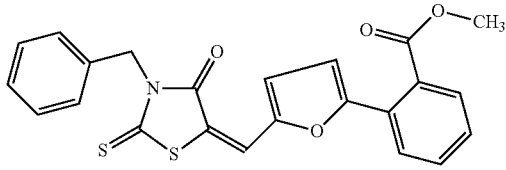 [SMILES: COC(=O)c1ccccc1-c1ccc(/C=C2/SC(=S)N(Cc3ccccc3)C2=O)o1]

(b) an organic compound functionally equivalent to compound C-13 having a molecular weight between 50 and 2500 Daltons, selected from substituted compounds of C-13, wherein one or more atoms belonging to a carbon chain, an aromatic group, a cycle or a heterocycle of C-13 substituted via a covalent bond by one or a plurality of halogens, and/or by one or a plurality of aromatic, cyclic, heterocyclic, alkyl, alkoxy, carboxyl, carbonyl, primary, secondary or tertiary amine, amide or sulphonamide groups; or
   (c) a stereo-isomer, racemate or pharmacologically acceptable salt of C-13 or of said functionally equivalent compound; wherein said functionally equivalent compound binds with Syk tyrosine kinase protein at a site located outside the catalytic domain of such protein, on a three-dimensional cavity situated between both SH2 domains and inter-domain A of Syk, wherein said three-dimensional cavity comprises the arginine residue situated in position 68 and the two glutamic acid residues situated in positions 121 and 155 of human Syk tyrosine kinase protein, the sequence of which is set forth in SEQ ID No: 1; and
   wherein said functionally equivalent compound is capable of inhibiting by at least 10% in vitro binding of antibody fragment G4G11 (SEQ) ID No: 2), with human Syk tyrosine kinase protein.

2. The method according to claim 1, wherein said three-dimensional cavity further comprises the serine residue situated in position 9, the glutamine residue situated in position 43, the phenylalanine residue situated in position 51, the isoleucine residue situated in position 66, the glutamate residues situated in positions 67 and 69, the leucine residue situated in position 70, the asparagine residue situated in position 71, the glycine residue situated in position 72, the threonine residue situated in position 73, the tyrosine residue situated in position 74 and the alanine residue situated in position 75.

3. The method according to claim 1, wherein said compound inhibits IgE-dependent mast cell degranulation.

4. The method according to claim 1, wherein said compound is capable of inhibiting, by 50% in vitro, mast cell degranulation at a concentration (IC50) between 1 ng/ml and 1 mg/ml.

5. The method according to claim 1, wherein said metabolic pathway involving Syk is a mast cell or basophil activation pathway.

6. The method according to claim 1, wherein said type I hypersensitivity reaction is allergic asthma, allergic conjunctivitis, allergic rhinitis, anaphylaxis, angioedema, urticaria, eosinophilia, or an allergy to an antibiotic.

7. The method according to claim 1, wherein said autoimmune disease is rheumatoid arthritis.

8. The method according to claim 1, wherein said compound is used in combination with a further therapeutic molecule.

9. The method according to claim 1, wherein said compound is administered orally, sublingually, nasally, ocularly, locally, intravenously, intraperitoneally, subcutaneously, by aerosol or by inhalation.

10. The method according to claim 1, wherein said compound is administered to an adult, a child or a newborn human patient.

11. The method according to claim 1, wherein said compound is administered at doses between 0.01 mg/kg and 200 mg/kg.

* * * * *

SEQUENCE LISTING

```
<160> NUMBER OF SEQ ID NOS: 4

<210> SEQ ID NO 1
<211> LENGTH: 635
<212> TYPE: PRT
<213> ORGANISM: Homo sapiens

<400> SEQUENCE: 1

Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
            20                  25                  30

Gly Met Ser Asp Gly Leu Tyr Leu Leu Arg Gln Ser Arg Asn Tyr Leu
        35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
    130                 135                 140
```

```
Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
    210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Thr Trp Ser Ala Gly Gly
        275                 280                 285

Ile Ile Ser Arg Ile Lys Ser Tyr Ser Phe Pro Lys Pro Gly His Arg
    290                 295                 300

Lys Ser Ser Pro Ala Gln Gly Asn Arg Gln Glu Ser Thr Val Ser Phe
305                 310                 315                 320

Asn Pro Tyr Glu Pro Glu Leu Ala Pro Trp Ala Ala Asp Lys Gly Pro
                325                 330                 335

Gln Arg Glu Ala Leu Pro Met Asp Thr Glu Val Tyr Glu Ser Pro Tyr
            340                 345                 350

Ala Asp Pro Glu Glu Ile Arg Pro Lys Glu Val Tyr Leu Asp Arg Lys
        355                 360                 365

Leu Leu Thr Leu Glu Asp Lys Glu Leu Gly Ser Gly Asn Phe Gly Thr
    370                 375                 380

Val Lys Lys Gly Tyr Tyr Gln Met Lys Lys Val Val Lys Thr Val Ala
385                 390                 395                 400

Val Lys Ile Leu Lys Asn Glu Ala Asn Asp Pro Ala Leu Lys Asp Glu
                405                 410                 415

Leu Leu Ala Glu Ala Asn Val Met Gln Gln Leu Asp Asn Pro Tyr Ile
            420                 425                 430

Val Arg Met Ile Gly Ile Cys Glu Ala Glu Ser Trp Met Leu Val Met
        435                 440                 445

Glu Met Ala Glu Leu Gly Pro Leu Asn Lys Tyr Leu Gln Gln Asn Arg
    450                 455                 460

His Val Lys Asp Lys Asn Ile Ile Glu Leu Val His Gln Val Ser Met
465                 470                 475                 480

Gly Met Lys Tyr Leu Glu Glu Ser Asn Phe Val His Arg Asp Leu Ala
                485                 490                 495

Ala Arg Asn Val Leu Leu Val Thr Gln His Tyr Ala Lys Ile Ser Asp
            500                 505                 510

Phe Gly Leu Ser Lys Ala Leu Arg Ala Asp Glu Asn Tyr Tyr Lys Ala
        515                 520                 525

Gln Thr His Gly Lys Trp Pro Val Lys Trp Tyr Ala Pro Glu Cys Ile
    530                 535                 540

Asn Tyr Tyr Lys Phe Ser Ser Lys Ser Asp Val Trp Ser Phe Gly Val
545                 550                 555                 560
```

```
Leu Met Trp Glu Ala Phe Ser Tyr Gly Gln Lys Pro Tyr Arg Gly Met
                565                 570                 575

Lys Gly Ser Glu Val Thr Ala Met Leu Glu Lys Gly Arg Met Gly
            580                 585                 590

Cys Pro Ala Gly Cys Pro Arg Glu Met Tyr Asp Leu Met Asn Leu Cys
                595                 600                 605

Trp Thr Tyr Asp Val Glu Asn Arg Pro Gly Phe Ala Ala Val Glu Leu
            610                 615                 620

Arg Leu Arg Asn Tyr Tyr Tyr Asp Val Val Asn
625                 630                 635

<210> SEQ ID NO 2
<211> LENGTH: 269
<212> TYPE: PRT
<213> ORGANISM: Artificial
<220> FEATURE:
<223> OTHER INFORMATION: antibody fragment G4G11

<400> SEQUENCE: 2

Met Ala Gln Val Gln Leu Gln Glu Ser Gly Pro Gly Leu Val Lys Pro
1               5                   10                  15

Ser Asp Thr Leu Ser Leu Thr Cys Ala Val Ser Gly Tyr Ser Ile Ser
            20                  25                  30

Ser Ser Asn Trp Trp Gly Trp Ile Arg Gln Pro Pro Gly Lys Gly Leu
        35                  40                  45

Glu Trp Ile Gly Tyr Ile Tyr His Ser Gly Ser Thr Tyr Tyr Asn Pro
    50                  55                  60

Ser Leu Lys Ser Arg Val Thr Ile Ser Val Asp Lys Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Asn Val Gly Phe His Asp Trp Gly Gln Gly Thr Leu
            100                 105                 110

Val Thr Val Ser Ser Gly Gly Gly Ser Gly Gly Gly Gly Ser Gly
        115                 120                 125

Gly Ser Ala Leu Gln Ser Val Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Ser Asn Tyr Val Tyr Trp Tyr Gln Gln Leu Pro Gly Thr Ala
                165                 170                 175

Pro Lys Leu Leu Ile Tyr Arg Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Arg Ser Glu Asp Glu Ala Asp Tyr Tyr Cys Ala Ala Trp
    210                 215                 220

Asp Asp Ser Leu Ala Ser Pro Val Phe Gly Gly Thr Lys Leu Thr
225                 230                 235                 240

Val Leu Gly Ala Ala Ala His His His His His Gly Ala Ala Glu
                245                 250                 255

Gln Lys Leu Ile Ser Glu Glu Asp Leu Asn Gly Ala Ala
            260                 265

<210> SEQ ID NO 3
<211> LENGTH: 269
```

```
<212> TYPE: PRT
<213> ORGANISM: Artificial
<220> FEATURE:
<223> OTHER INFORMATION: antibody fragment G4E4

<400> SEQUENCE: 3

Met Ala Gln Val Gln Leu Gln Glu Ser Gly Pro Gly Leu Val Lys Pro
1               5                   10                  15

Ser Asp Thr Leu Ser Leu Thr Cys Ala Val Ser Gly Tyr Ser Ile Ser
            20                  25                  30

Ser Ser Asn Trp Trp Gly Trp Ile Arg Gln Pro Pro Gly Lys Gly Leu
        35                  40                  45

Glu Trp Ile Gly Tyr Ile Tyr His Ser Gly Ser Thr Tyr Tyr Asn Pro
50                  55                  60

Ser Leu Lys Ser Arg Val Thr Ile Ser Val Asp Lys Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Asn Val Gly Phe His Asp Trp Gly Gln Gly Thr Leu
            100                 105                 110

Val Thr Val Ser Gly Gly Gly Gly Ser Gly Gly Gly Gly Ser Gly
        115                 120                 125

Gly Ser Ala Leu Gln Ser Val Leu Thr Gln Pro Pro Ser Ala Ser Gly
130                 135                 140

Thr Pro Gly Gln Arg Val Thr Ile Ser Cys Ser Gly Ser Ser Ser Asn
145                 150                 155                 160

Ile Gly Ser Asn Thr Val Asn Trp Tyr Gln Gln Leu Pro Gly Thr Ala
                165                 170                 175

Pro Lys Leu Leu Ile Tyr Ser Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Gln Ser Glu Asp Glu Ala Asp Tyr Tyr Cys Ala Ala Trp
210                 215                 220

Asp Asp Ser Leu Phe Gly Ala Val Phe Gly Gly Gly Thr Lys Leu Thr
225                 230                 235                 240

Val Leu Gly Ala Ala Ala His His His His His Gly Ala Ala Glu
                245                 250                 255

Gln Lys Leu Ile Ser Glu Glu Asp Leu Asn Gly Ala Ala
            260                 265

<210> SEQ ID NO 4
<211> LENGTH: 629
<212> TYPE: PRT
<213> ORGANISM: Mus musculus

<400> SEQUENCE: 4

Met Ala Gly Ser Ala Val Asp Ser Ala Asn His Leu Thr Tyr Phe Phe
1               5                   10                  15

Gly Asn Ile Thr Arg Glu Glu Ala Glu Asp Tyr Leu Val Gln Gly Gly
            20                  25                  30

Met Thr Asp Gly Leu Tyr Leu Leu Arg Gln Ser Arg Asn Tyr Leu Gly
        35                  40                  45

Gly Phe Ala Leu Ser Val Ala His Asn Arg Lys Ala His His Tyr Thr
50                  55                  60

Ile Glu Arg Glu Leu Asn Gly Thr Tyr Ala Ile Ser Gly Gly Arg Ala
```

-continued

```
                65                  70                  75                  80
His Ala Ser Pro Ala Asp Leu Cys His Tyr His Ser Gln Glu Pro Asp
                    85                  90                  95

Gly Leu Ile Cys Leu Leu Lys Lys Pro Phe Asn Arg Pro Pro Gly Val
                    100                 105                 110

Gln Pro Lys Thr Gly Pro Phe Glu Asp Leu Lys Glu Asn Leu Ile Arg
                    115                 120                 125

Glu Tyr Val Lys Gln Thr Trp Asn Leu Gln Gly Gln Ala Leu Glu Gln
            130                 135                 140

Ala Ile Ile Ser Gln Lys Pro Gln Leu Glu Lys Leu Ile Ala Thr Thr
145                 150                 155                 160

Ala His Glu Lys Met Pro Trp Phe His Gly Asn Ile Ser Arg Asp Glu
                    165                 170                 175

Ser Glu Gln Thr Val Leu Ile Gly Ser Lys Thr Asn Gly Lys Phe Leu
            180                 185                 190

Ile Arg Ala Arg Asp Asn Ser Gly Ser Tyr Ala Leu Cys Leu Leu His
                195                 200                 205

Glu Gly Lys Val Leu His Tyr Arg Ile Asp Arg Asp Lys Thr Gly Lys
        210                 215                 220

Leu Ser Ile Pro Glu Gly Lys Lys Phe Asp Thr Leu Trp Gln Leu Val
225                 230                 235                 240

Glu His Tyr Ser Tyr Lys Pro Asp Gly Leu Leu Arg Val Leu Thr Val
                    245                 250                 255

Pro Cys Gln Lys Ile Gly Ala Gln Met Gly His Pro Gly Ser Pro Asn
                260                 265                 270

Ala His Pro Val Thr Trp Ser Pro Gly Gly Ile Ile Ser Arg Ile Lys
            275                 280                 285

Ser Tyr Ser Phe Pro Lys Pro Gly His Lys Lys Pro Ala Pro Pro Gln
        290                 295                 300

Gly Ser Arg Pro Glu Ser Thr Val Ser Phe Asn Pro Tyr Glu Pro Thr
305                 310                 315                 320

Gly Gly Pro Trp Gly Pro Asp Arg Gly Leu Gln Arg Glu Ala Leu Pro
                    325                 330                 335

Met Asp Thr Glu Val Tyr Glu Ser Pro Tyr Ala Asp Pro Glu Glu Ile
                340                 345                 350

Arg Pro Lys Glu Val Tyr Leu Asp Arg Ser Leu Leu Thr Leu Glu Asp
            355                 360                 365

Asn Glu Leu Gly Ser Gly Asn Phe Gly Thr Val Lys Lys Gly Tyr Tyr
        370                 375                 380

Gln Met Lys Lys Val Val Lys Thr Val Ala Val Lys Ile Leu Lys Asn
385                 390                 395                 400

Glu Ala Asn Asp Pro Ala Leu Lys Asp Glu Leu Leu Ala Glu Ala Asn
                    405                 410                 415

Val Met Gln Gln Leu Asp Asn Pro Tyr Ile Val Arg Met Ile Gly Ile
                420                 425                 430

Cys Glu Ala Glu Ser Trp Met Leu Val Met Glu Met Ala Glu Leu Gly
            435                 440                 445

Pro Leu Asn Lys Tyr Leu Gln Gln Asn Arg His Ile Lys Asp Lys Asn
        450                 455                 460

Ile Ile Glu Leu Val His Gln Val Ser Met Gly Met Lys Tyr Leu Glu
465                 470                 475                 480

Glu Ser Asn Phe Val His Arg Asp Leu Ala Ala Arg Asn Val Leu Leu
                    485                 490                 495
```

```
Val Thr Gln His Tyr Ala Lys Ile Ser Asp Phe Gly Leu Ser Lys Ala
            500                 505                 510

Leu Arg Ala Asp Glu Asn Tyr Tyr Lys Ala Gln Thr His Gly Lys Trp
            515                 520                 525

Pro Val Lys Trp Tyr Ala Pro Glu Cys Ile Asn Tyr Tyr Lys Phe Ser
            530                 535                 540

Ser Lys Ser Asp Val Trp Ser Phe Gly Val Leu Met Trp Glu Ala Phe
545                 550                 555                 560

Ser Tyr Gly Gln Lys Pro Tyr Arg Gly Met Lys Gly Ser Glu Val Thr
                565                 570                 575

Ala Met Leu Glu Lys Gly Glu Arg Met Gly Cys Pro Ala Gly Cys Pro
            580                 585                 590

Arg Glu Met Tyr Asp Leu Met Asn Leu Cys Trp Thr Tyr Asp Val Glu
            595                 600                 605

Asn Arg Pro Gly Phe Thr Ala Val Glu Leu Arg Leu Arg Asn Tyr Tyr
            610                 615                 620

Tyr Asp Val Val Asn
625
```